US011024419B2

(12) United States Patent
Kamen et al.

(10) Patent No.: US 11,024,419 B2
(45) Date of Patent: *Jun. 1, 2021

(54) SYSTEM, METHOD, AND APPARATUS FOR ESTIMATING LIQUID DELIVERY

(71) Applicant: DEKA Products Limited Partnership, Manchester, NH (US)

(72) Inventors: Dean Kamen, Bedford, NH (US); John M. Kerwin, Manchester, NH (US); Colin H. Murphy, Cambridge, MA (US)

(73) Assignee: DEKA Products Limited Partnership, Manchester, NH (US)

( * ) Notice: Subject to any disclaimer, the term of this patent is extended or adjusted under 35 U.S.C. 154(b) by 71 days.

This patent is subject to a terminal disclaimer.

(21) Appl. No.: 16/241,239

(22) Filed: Jan. 7, 2019

(65) Prior Publication Data

US 2019/0134298 A1 May 9, 2019

Related U.S. Application Data

(63) Continuation of application No. 15/467,196, filed on Mar. 23, 2017, now Pat. No. 10,220,135, which is a
(Continued)

(51) Int. Cl.
*A61M 5/142* (2006.01)
*G16H 40/60* (2018.01)
(Continued)

(52) U.S. Cl.
CPC ............ *G16H 40/60* (2018.01); *A61M 5/142* (2013.01); *A61M 5/1452* (2013.01);
(Continued)

(58) Field of Classification Search
CPC .......... A61M 5/16809; A61M 5/16813; A61M 5/1452; A61M 5/168; A61M 5/1684;
(Continued)

(56) References Cited

U.S. PATENT DOCUMENTS

| 4,991,433 A | 2/1991 | Warnaka |
| 5,349,852 A | 9/1994 | Kamen et al. |

(Continued)

FOREIGN PATENT DOCUMENTS

| EP | 467657 A1 | 1/1992 |
| JP | 2008515600 A | 5/2008 |

(Continued)

OTHER PUBLICATIONS

J81WO International Search Report and Written Opinion dated Jul. 31, 2013, received in International patent application No. PCT/US2012/071112, 17 pgs.

(Continued)

*Primary Examiner* — William R Carpenter
(74) *Attorney, Agent, or Firm* — James D. Wyninegar, Jr.

(57) ABSTRACT

A pump includes a reservoir, a port, and a plunger. The reservoir delivers a liquid by discharging the liquid through the port coupled to the reservoir. A piston of the plunger defines a liquid side of the reservoir and a non-liquid side of the reservoir whereby movement of the plunger towards the liquid side of the reservoir discharges liquid through the port. The pump also includes a reference-volume assembly and/or a linear position sensor. The reference-volume assembly is coupled to the reservoir at an opposite end of the reservoir relative to the port and includes a reference-volume chamber in acoustic communication with the non-liquid side of the reservoir, a speaker disposed within the reference-volume chamber, and a reference microphone disposed within the reference-volume chamber. The pump estimate the amount of liquid discharged from the reservoir.

20 Claims, 12 Drawing Sheets

Related U.S. Application Data continuation of application No. 13/723,251, filed on Dec. 21, 2012, now Pat. No. 9,636,455, which is a continuation-in-part of application No. 13/333,574, filed on Dec. 21, 2011, now Pat. No. 10,453,157, and a continuation-in-part of application No. PCT/US2011/066588, filed on Dec. 21, 2011.

(60) Provisional application No. 61/679,117, filed on Aug. 3, 2012, provisional application No. 61/651,322, filed on May 24, 2012, provisional application No. 61/578,649, filed on Dec. 21, 2011, provisional application No. 61/578,658, filed on Dec. 21, 2011, provisional application No. 61/578,674, filed on Dec. 21, 2011.

(51) Int. Cl.
  *A61M 5/168* (2006.01)
  *A61M 5/145* (2006.01)
  *G16H 20/17* (2018.01)
  *G01F 23/296* (2006.01)

(52) U.S. Cl.
  CPC .......... *A61M 5/1684* (2013.01); *G01F 23/296* (2013.01); *G16H 20/17* (2018.01); *A61M 2205/18* (2013.01); *A61M 2205/3306* (2013.01); *A61M 2205/3375* (2013.01); *A61M 2205/3379* (2013.01); *A61M 2205/3592* (2013.01); *A61M 2205/50* (2013.01); *A61M 2205/581* (2013.01); *A61M 2205/582* (2013.01); *A61M 2205/6054* (2013.01); *A61M 2205/6072* (2013.01)

(58) Field of Classification Search
  CPC .. A61M 2205/3375; A61M 2205/3379; A61M 2205/3382; A61M 2205/3389
  See application file for complete search history.

(56) References Cited

U.S. PATENT DOCUMENTS

| | | | |
|---|---|---|---|
| 5,575,310 A | 11/1996 | Kamen et al. | |
| 6,070,761 A | 6/2000 | Bloom | |
| 6,305,541 B1 | 10/2001 | Tanner et al. | |
| 7,021,560 B2 | 4/2006 | Gray | |
| 7,066,029 B2 | 6/2006 | Beavis | |
| 7,146,977 B2 | 12/2006 | Beavis | |
| 7,305,984 B2 | 12/2007 | Altobelli | |
| 7,342,660 B2 | 3/2008 | Altobelli | |
| 7,548,314 B2 | 6/2009 | Altobelli | |
| 7,806,116 B2 | 10/2010 | Altobelli | |
| 8,087,303 B2 | 1/2012 | Beavis | |
| 8,113,244 B2 | 2/2012 | Kamen | |
| 8,303,574 B2 | 11/2012 | Gray | |
| 8,414,522 B2 | 4/2013 | Kamen | |
| 8,414,563 B2 | 4/2013 | Kamen | |
| 8,435,214 B2 | 5/2013 | Gray | |
| 8,486,018 B2 | 7/2013 | Kamen | |
| 8,491,570 B2 | 7/2013 | Kamen | |
| 8,496,646 B2 | 7/2013 | Kamen | |
| 8,545,445 B2 | 10/2013 | Kamen | |
| 8,585,377 B2 | 11/2013 | Kamen | |
| D728,779 S | 5/2015 | Sabin et al. | |
| D735,319 S | 7/2015 | Sabin et al. | |
| D736,370 S | 8/2015 | Sabin et al. | |
| 9,151,646 B2 | 10/2015 | Kamen et al. | |
| D745,661 S | 12/2015 | Collins et al. | |
| D749,206 S | 2/2016 | Johnson et al. | |
| 9,248,233 B2 | 2/2016 | Kamen et al. | |
| 9,265,879 B2 | 2/2016 | Gray | |
| D751,689 S | 3/2016 | Peret et al. | |
| D751,690 S | 3/2016 | Peret et al. | |
| D752,209 S | 3/2016 | Peret et al. | |
| 9,295,778 B2 | 3/2016 | Kamen et al. | |
| 9,295,779 B2 | 3/2016 | Kamen et al. | |
| D754,065 S | 4/2016 | Gray et al. | |
| D756,386 S | 5/2016 | Kendler et al. | |
| D758,399 S | 6/2016 | Kendler et al. | |
| D760,288 S | 6/2016 | Kendler et al. | |
| D760,289 S | 6/2016 | Kendler et al. | |
| 9,364,394 B2 | 6/2016 | Demers et al. | |
| 9,372,486 B2 | 6/2016 | Peret et al. | |
| D760,782 S | 7/2016 | Kendler et al. | |
| D760,888 S | 7/2016 | Gill et al. | |
| 9,400,873 B2 | 7/2016 | Kamen et al. | |
| 9,408,966 B2 | 8/2016 | Kamen | |
| D767,756 S | 9/2016 | Sabin | |
| 9,435,455 B2 | 9/2016 | Peret et al. | |
| D768,716 S | 10/2016 | Kendler et al. | |
| 9,465,919 B2 | 10/2016 | Kamen et al. | |
| 9,488,200 B2 | 11/2016 | Kamen et al. | |
| D774,645 S | 12/2016 | Gill et al. | |
| 9,518,958 B2 | 12/2016 | Wilt et al. | |
| 9,636,455 B2 | 5/2017 | Kamen et al. | |
| D789,516 S | 6/2017 | Gill et al. | |
| 9,675,756 B2 | 6/2017 | Kamen et al. | |
| 9,677,555 B2 | 6/2017 | Kamen et al. | |
| 9,687,417 B2 | 6/2017 | Demers et al. | |
| D792,963 S | 7/2017 | Gill | |
| D795,424 S | 8/2017 | Sloss | |
| D795,805 S | 8/2017 | Gray et al. | |
| 9,719,964 B2 | 8/2017 | Blumberg | |
| 9,724,465 B2 | 8/2017 | Peret et al. | |
| 9,724,466 B2 | 8/2017 | Peret et al. | |
| 9,724,467 B2 | 8/2017 | Peret et al. | |
| 9,730,731 B2 | 8/2017 | Langenfeld et al. | |
| 9,744,300 B2 | 8/2017 | Kamen et al. | |
| 9,746,093 B2 | 8/2017 | Peret et al. | |
| 9,746,094 B2 | 8/2017 | Peret et al. | |
| 9,759,343 B2 | 9/2017 | Peret et al. | |
| 9,759,369 B2 | 9/2017 | Gray et al. | |
| 9,772,044 B2 | 9/2017 | Peret et al. | |
| D799,025 S | 10/2017 | Johnson et al. | |
| D801,519 S | 10/2017 | Sabin et al. | |
| 9,789,247 B2 | 10/2017 | Kamen et al. | |
| D802,118 S | 11/2017 | Peret et al. | |
| D803,386 S | 11/2017 | Sabin et al. | |
| D803,387 S | 11/2017 | Bodwell et al. | |
| D804,017 S | 11/2017 | Sabin | |
| 9,808,572 B2 | 11/2017 | Kamen et al. | |
| D805,183 S | 12/2017 | Sabin et al. | |
| 9,856,990 B2 | 1/2018 | Peret et al. | |
| D813,376 S | 3/2018 | Peret et al. | |
| D814,021 S | 3/2018 | Sabin | |
| D815,730 S | 4/2018 | Collins et al. | |
| D816,685 S | 5/2018 | Kendler et al. | |
| D816,829 S | 5/2018 | Peret et al. | |
| D817,479 S | 5/2018 | Sabin et al. | |
| D817,480 S | 5/2018 | Sabin et al. | |
| 9,968,730 B2 | 5/2018 | Blumberg, Jr. et al. | |
| 9,976,665 B2 | 5/2018 | Peret et al. | |
| 10,044,791 B2 | 8/2018 | Kamen et al. | |
| 10,220,135 B2 * | 3/2019 | Kamen | G16H 20/17 |
| 2005/0066735 A1 | 3/2005 | Beavis | |
| 2005/0066962 A1 | 3/2005 | Altobelli | |
| 2005/0066963 A1 | 3/2005 | Beavis | |
| 2005/0067511 A1 | 3/2005 | Gray | |
| 2005/0068528 A1 | 3/2005 | Altobelli | |
| 2007/0219480 A1 | 9/2007 | Kamen | |
| 2007/0219496 A1 | 9/2007 | Kamen | |
| 2007/0219597 A1 | 9/2007 | Kamen | |
| 2007/0228071 A1 | 10/2007 | Kamen | |
| 2008/0212094 A1 | 9/2008 | Altobelli | |
| 2008/0295826 A1 | 12/2008 | Altobelli | |
| 2009/0213373 A1 | 8/2009 | Altobelli | |
| 2009/0254037 A1 | 10/2009 | Bryant, Jr. | |
| 2009/0275896 A1 | 11/2009 | Kamen | |
| 2009/0281497 A1 | 11/2009 | Kamen | |
| 2009/0299277 A1 | 12/2009 | Kamen | |
| 2009/0299289 A1 | 12/2009 | Kamen | |
| 2010/0005903 A1 | 1/2010 | Beavis | |

(56) References Cited

U.S. PATENT DOCUMENTS

| | | |
|---|---|---|
| 2010/0185142 A1 | 7/2010 | Kamen |
| 2010/0185175 A1 | 7/2010 | Kamen |
| 2010/0191186 A1 | 7/2010 | Blumberg, Jr. |
| 2010/0198182 A1 | 8/2010 | Lanigan |
| 2010/0198183 A1 | 8/2010 | Lanigan |
| 2011/0029260 A1 | 2/2011 | Altobelli |
| 2011/0040247 A1 | 2/2011 | Mandro |
| 2011/0047499 A1 | 2/2011 | Mandro |
| 2011/0079220 A1 | 4/2011 | Altobelli |
| 2011/0144574 A1 | 6/2011 | Kamen |
| 2011/0144616 A1 | 6/2011 | Michaud et al. |
| 2011/0186177 A1 | 8/2011 | Lanier, Jr. |
| 2011/0190694 A1 | 8/2011 | Lanier, Jr. |
| 2011/0300001 A1 | 12/2011 | Murphy |
| 2011/0306931 A1 | 12/2011 | Kamen |
| 2011/0313351 A1 | 12/2011 | Kamen |
| 2011/0313789 A1 | 12/2011 | Kamen |
| 2011/0319813 A1 | 12/2011 | Kamen |
| 2012/0035543 A1 | 2/2012 | Kamen |
| 2012/0150115 A1 | 6/2012 | Kamen |
| 2012/0185267 A1 | 7/2012 | Kamen |
| 2012/0192969 A1 | 8/2012 | Beavis |
| 2012/0203177 A1 | 8/2012 | Lanier, Jr. |
| 2012/0204996 A1 | 8/2012 | Gray |
| 2012/0209178 A1 | 8/2012 | Gray |
| 2012/0209179 A1 | 8/2012 | Kamen |
| 2012/0209180 A1 | 8/2012 | Gray |
| 2012/0209181 A1 | 8/2012 | Gray |
| 2012/0209182 A1 | 8/2012 | Gray |
| 2012/0209183 A1 | 8/2012 | Gray |
| 2012/0209184 A1 | 8/2012 | Kamen |
| 2012/0209185 A1 | 8/2012 | Kamen |
| 2012/0209186 A1 | 8/2012 | Kamen |
| 2012/0209187 A1 | 8/2012 | Kamen |
| 2012/0209188 A1 | 8/2012 | Gray |
| 2012/0209189 A1 | 8/2012 | Gray |
| 2012/0209190 A1 | 8/2012 | Gray |
| 2012/0209191 A1 | 8/2012 | Gray |
| 2012/0209193 A1 | 8/2012 | Gray |
| 2012/0209195 A1 | 8/2012 | Kamen |
| 2012/0209198 A1 | 8/2012 | Gray |
| 2012/0209199 A1 | 8/2012 | Kamen |
| 2012/0209204 A1 | 8/2012 | Gray |
| 2012/0209207 A1 | 8/2012 | Gray |
| 2012/0209209 A1 | 8/2012 | Kamen |
| 2012/0209217 A1 | 8/2012 | Gray |
| 2012/0209219 A1 | 8/2012 | Kamen |
| 2012/0209239 A1 | 8/2012 | Gray |
| 2012/0209240 A1 | 8/2012 | Gray |
| 2012/0209244 A1 | 8/2012 | Gray |
| 2012/0238851 A1 | 9/2012 | Kamen |
| 2013/0177455 A1 | 7/2013 | Kamen |
| 2013/0182381 A1 | 7/2013 | Gray |
| 2013/0184676 A1 | 7/2013 | Kamen |
| 2013/0188040 A1 | 7/2013 | Kamen |
| 2013/0191513 A1 | 7/2013 | Kamen |
| 2013/0197693 A1 | 8/2013 | Kamen |
| 2013/0204188 A1 | 8/2013 | Kamen |
| 2013/0272773 A1 | 10/2013 | Kamen |
| 2013/0281965 A1 | 10/2013 | Kamen |
| 2013/0297330 A1 | 11/2013 | Kamen |
| 2013/0310990 A1 | 11/2013 | Peret |
| 2013/0317753 A1 | 11/2013 | Kamen |
| 2013/0317837 A1 | 11/2013 | Ballantyne |
| 2013/0336814 A1 | 12/2013 | Kamen |
| 2013/0339049 A1 | 12/2013 | Blumberg, Jr. |
| 2013/0346108 A1 | 12/2013 | Kamen |
| 2014/0165703 A1 | 6/2014 | Wilt |
| 2014/0180711 A1 | 6/2014 | Kamen |
| 2014/0188076 A1 | 7/2014 | Kamen |
| 2014/0188516 A1 | 7/2014 | Kamen |
| 2014/0195639 A1 | 7/2014 | Kamen |
| 2014/0227021 A1 | 8/2014 | Kamen |
| 2014/0318639 A1 | 10/2014 | Peret |
| 2014/0343492 A1 | 11/2014 | Kamen |
| 2015/0002667 A1 | 1/2015 | Peret et al. |
| 2015/0002668 A1 | 1/2015 | Peret et al. |
| 2015/0002677 A1 | 1/2015 | Peret et al. |
| 2015/0033823 A1 | 2/2015 | Blumberg, Jr. |
| 2015/0154364 A1 | 6/2015 | Biasi et al. |
| 2015/0157791 A1 | 6/2015 | Desch et al. |
| 2015/0238228 A1 | 8/2015 | Langenfeld et al. |
| 2015/0257974 A1 | 9/2015 | Demers et al. |
| 2015/0314083 A1 | 11/2015 | Blumberg, Jr. et al. |
| 2015/0332009 A1 | 11/2015 | Kane et al. |
| 2016/0055397 A1 | 2/2016 | Peret et al. |
| 2016/0055649 A1 | 2/2016 | Peret et al. |
| 2016/0061641 A1 | 3/2016 | Peret et al. |
| 2016/0063353 A1 | 3/2016 | Peret et al. |
| 2016/0073063 A1 | 3/2016 | Peret et al. |
| 2016/0084434 A1 | 3/2016 | Janway et al. |
| 2016/0097382 A1 | 4/2016 | Kamen et al. |
| 2016/0131272 A1 | 5/2016 | Yoo |
| 2016/0158437 A1 | 6/2016 | Biasi et al. |
| 2016/0179086 A1 | 6/2016 | Peret et al. |
| 2016/0184510 A1 | 6/2016 | Kamen et al. |
| 2016/0203292 A1 | 7/2016 | Kamen et al. |
| 2016/0262977 A1 | 9/2016 | Demers et al. |
| 2016/0319850 A1 | 11/2016 | Kamen et al. |
| 2016/0346056 A1 | 12/2016 | Demers et al. |
| 2016/0362234 A1 | 12/2016 | Peret et al. |
| 2017/0011202 A1 | 1/2017 | Kamen et al. |
| 2017/0045478 A1 | 2/2017 | Wilt et al. |
| 2017/0216516 A1 | 8/2017 | Dale et al. |
| 2017/0224909 A1 | 8/2017 | Kamen et al. |
| 2017/0259230 A1 | 9/2017 | Demers et al. |
| 2017/0266378 A1 | 9/2017 | Kamen et al. |
| 2017/0268497 A1 | 9/2017 | Kamen et al. |
| 2017/0284968 A1 | 10/2017 | Blumberg, Jr. |
| 2017/0296745 A1 | 10/2017 | Kamen et al. |
| 2017/0303969 A1 | 10/2017 | Langenfeld et al. |
| 2017/0321841 A1 | 11/2017 | Gray et al. |
| 2017/0333623 A1 | 11/2017 | Kamen et al. |
| 2017/0335988 A1 | 11/2017 | Peret et al. |
| 2018/0038501 A1 | 2/2018 | Peret et al. |
| 2018/0066648 A1 | 3/2018 | Kamen et al. |
| 2018/0080605 A1 | 3/2018 | Janway et al. |
| 2018/0106246 A1 | 4/2018 | Kamen et al. |
| 2018/0128259 A1 | 5/2018 | Kamen et al. |

FOREIGN PATENT DOCUMENTS

| | | |
|---|---|---|
| JP | 2008540117 A | 11/2008 |
| JP | 2009525825 A | 7/2009 |
| JP | A2009525825 | 7/2009 |
| JP | A2008515600 | 5/2015 |
| WO | WO0018298 A1 | 4/2000 |
| WO | WO2006044341 A2 | 4/2006 |
| WO | WO2006124634 A1 | 11/2006 |
| WO | WO2007092618 A2 | 8/2007 |
| WO | WO2009039203 A2 | 3/2009 |
| WO | WO2010111505 A2 | 9/2010 |
| WO | WO2011032960 A1 | 3/2011 |
| WO | WO2013095459 A1 | 6/2013 |
| WO | WO2013095459 A9 | 6/2013 |
| WO | WO2013096713 A2 | 6/2013 |
| WO | WO2013096718 A2 | 6/2013 |
| WO | WO2013096722 A2 | 6/2013 |
| WO | WO2013096789 A1 | 6/2013 |
| WO | WO2013096909 A2 | 6/2013 |
| WO | WO2013176770 A2 | 11/2013 |
| WO | WO2013177357 A1 | 11/2013 |
| WO | WO2014100557 A2 | 6/2014 |
| WO | WO2014100571 A2 | 6/2014 |
| WO | WO2014100658 A1 | 6/2014 |
| WO | WO2014100687 A2 | 6/2014 |
| WO | WO2014100736 A2 | 6/2014 |
| WO | WO2014100744 A2 | 6/2014 |
| WO | WO2014144557 A2 | 9/2014 |
| WO | WO2015017275 A1 | 2/2015 |

(56) References Cited

OTHER PUBLICATIONS

Notice for Reason for Rejection, dated Jun. 23, 2015, received in Japanese patent application National Publication No. 2014-548929, 5 pgs.
Final Notice for Reason for Rejection, dated Feb. 9, 2016, received in Japanese patent application National Publication No. 2014-548929, 4 pgs.
European Search Report dated Jun. 6, 2016, received in European patent application No. 12826613.7-1662, 4 pgs.
Decision of Rejection for Japanese Patent Application 2014-548929, 6 pgs. dated Nov. 1, 2016.
Communication of substantive examination report for Mexican Patent Application MX/a2014/007749, 2 pgs. dated Sep. 6, 2016.
Response to European Search Report of dated Jun. 6 2016, received in European patent application No. 12826613.7-1662 (J81EP), response submitted on Oct. 17, 2016, 12 pgs.
Communication pursuant to Rules 161 and 162 EPC in EP Patent Appln. 12826613.7-1662, dated Aug. 18, 2014, 2 pgs.
Response to Communication pursuant to Rules 161 and 162 EPC in EP Patent Appln. 12826613.7-1662 dated Aug. 18, 2014, submitted on Jan. 14, 2015, 27 pgs.
Pretrial Re-Examination Report for Japanese Patent Application No. 2014-548929, 5 pgs. dated May 23, 2017.
European Examination Report under Article 94(3) EPC, dated Jun. 27, 2017, received in European patent application No. 12826613.7-1664, 5 pgs.
Notice for Reason for Rejection, dated Oct. 24, 2017, received in Japanese patent application National Publication No. 2017-038304, 4 pgs. Translation 5 pgs.
Notice for Reason for Rejection, dated Jul. 4, 2017, received in Japanese patent application National Publication No. 2017-038304, 5 pgs. Translation 6 pgs.
Notice for Reason for Rejection, dated Feb. 27, 2018, received in Japanese patent application National Publication No. 2017-038304, 2 pgs. Translation 1 pgs.
Extended European Search Report dated Jun. 28, 2017, received in European patent application No. 17168091.1-1664, 10 pgs.
U.S. Appl. No. 61/578,658, filed Dec. 21, 2011.
U.S. Appl. No. PCT/US12/71112, filed Dec. 21, 2012, WO2013096713A1.
U.S. Appl. No. 13/723,251, filed Dec. 21, 2012, US20130204188A1
U.S. Appl. No. 15/467,196, filed Mar. 23, 2017, US20170224909A1.
U.S. Appl. No. 15/467,196, filed Mar. 23, 2017.
U.S. Appl. No. 13/723,251, filed Dec. 21, 2012.
B2, JP2008515600A, WO2006/044341A2.
B3, JP2008540117A, WO2006/124634A1.
B4, JP2009525825A, WO2007/092618A2.
B5, JPA2008515600, WO2006/044341.
B6, JPA2009525825, WO2007/092618A2.
Notice for Reason for Rejection, dated Jun. 23, 2015, received in Japanese patent application National Publication No. 2014-548929, 5 pgs. English Translation.
Final Notice for Reason for Rejection, dated Feb. 9, 2016, received in Japanese. English Translation.
Decision of Rejection for Japanese Patent Application 2014-548929, 6 pgs. dated Nov. 1, 2016. English Translation.
Communication of substantive examination report for Mexican Patent Application MX/a2014/007749, 2 pg. dated Sep. 6, 2016. English Translation.
Pretrial Re-Exmaination Report for Japanese Patent Application No. 2014-548929, 5 pgs. dated May 23, 2017. English Translation.
Notice for Reason for Rejection, dated Oct. 24, 2017, received in English Partial Translation.
Notice for Reason for Rejection, dated Jul. 4, 2017, received in Japanese patentn application National Publication No. 2017-038304, 5 pgs. Translation 6 pgs. Partial English Translation.
Notice for Reason for Rejection, dated Feb. 27, 2018, received in Japanese patent application National Publication No. 2017-038304, 2 pgs. Translation 1 pgs. English Translation.

\* cited by examiner

SYSTEM, METHOD, AND APPARATUS FOR ESTIMATING LIQUID DELIVERY

CROSS REFERENCE TO RELATED APPLICATIONS

This application is a continuation of U.S. patent application Ser. No. 15/467,196, filed Mar. 23, 2017 and entitled System, Method, and Apparatus for Estimating Liquid Delivery, now U.S. Publication No. US 2017-0224909-A1, published Aug. 10, 2017, which is a continuation of U.S. patent application Ser. No. 13/723,251, filed Dec. 21, 2012 and entitled System, Method, and Apparatus for Estimating Liquid Delivery, now U.S. Pat. No. 9,636,455, issued May 2, 2017 which is a Non-Provisional which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method and Apparatus for Estimating Liquid Delivery;

U.S. Provisional Patent Application Ser. No. 61/578,674, filed Dec. 21, 2011 and entitled System, Method and Apparatus for Dispensing Oral Medications);

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

U.S. patent application Ser. No. 13/723,251, filed Dec. 21, 2012 and entitled System, Method, and Apparatus for Estimating Liquid Delivery, now U.S. Pat. No. 9,636,455, issued May 2, 2017 claims priority to, benefit of, and is also a Continuation-In-Part application of the following:

U.S. patent application Ser. No. 13/333,574, filed Dec. 21, 2011 and entitled System, Method, and Apparatus for Electronic Patient Care, now U.S. Publication No. US 2012-0185267-A1, published Jul. 19, 2012, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 15/467,196, filed Mar. 23, 2017 and entitled System, Method, and Apparatus for Estimating Liquid Delivery, now U.S. Publication No. US 2017-0224909-A1, published Aug. 10, 2017 may also be related to one or more of the following patent applications filed on even date herewith, all of which are hereby incorporated herein by reference in their entireties:

U.S. patent application Ser. No. 13/723,238, filed Dec. 21, 2012 and entitled System, Method, and Apparatus for Clamping, now U.S. Pat. No. 9,759,369, issued Sep. 12, 2017;

U.S. patent application Ser. No. 13/723,235, filed Dec. 21, 2012, and entitled System, Method, and Apparatus for Dispensing Oral Medications, now U.S. Pat. No. 9,400,873, issued Jul. 26, 2016;

PCT Application Serial No. PCT/US12/71131, filed Dec. 21, 2012 and entitled System, Method, and Apparatus for Dispensing Oral Medications;

U.S. patent application Ser. No. 13/724,568, filed Dec. 21, 2012 and entitled Syringe Pump, now U.S. Pat. No. 9,295,778, issued Mar. 29, 2016;

U.S. patent application Ser. No. 13/725,790, filed Dec. 21, 2012 and entitled System, Method, and Apparatus for Infusing Fluid, now U.S. Pat. No. 9,677,555, issued Jun. 13, 2017;

PCT Application Serial No. PCT/US12/71490, filed Dec. 21, 2012 and entitled System, Method, and Apparatus for Infusing Fluid;

U.S. patent application Ser. No. 13/723,239, filed Dec. 21, 2012 and entitled System, Method, and Apparatus for Electronic Patient Care, now U.S. Pat. No. 10,108,785, issued Oct. 23, 2018;

U.S. patent application Ser. No. 13/723,242, filed Dec. 21, 2012 and entitled System, Method, and Apparatus for Electronic Patient Care, now U.S. Publication No. US 2013-0317753-A1, published Nov. 28, 2013;

U.S. patent application Ser. No. 13/723,244, filed Dec. 21, 2012 and entitled System, Method, and Apparatus for Monitoring, Regulating, or Controlling Fluid Flow, now U.S. Pat. No. 9,151,646, issued Oct. 6, 2015;

PCT Application No. PCT/US12/71142, filed Dec. 21, 2012 and entitled System, Method, and Apparatus for Monitoring, Regulating, or Controlling Fluid Flow;

PCT Application No. PCT/US12/71112, filed Dec. 21, 2012 and entitled System, Method, and Apparatus for Estimating Liquid Delivery; and U.S. application Ser. No. 13/723,253, field Dec. 21, 2012 and entitled System, Method, and Apparatus for Electronic Patient Care, now U.S. Publication No. US 2013-0191513-A1, published Jul. 25, 2013.

BACKGROUND

Relevant Field

The present disclosure relates to pumps. More particularly, the present disclosure relates to a system, method, and apparatus for liquid delivery using a syringe pump.

Description of Related Art

Syringe pumps are used in a variety of medical applications, such as for intravenous delivery of liquid medications, for example a patient in an intensive-care unit (ICU), for an extended length of time. Syringe pumps may be designed so that needles, tubing, or other attachments are attachable to the syringe pump. Syringe pumps typically include a plunger mounted to a shaft that pushes a liquid out of a reservoir. The reservoir may be a tube-shaped structure having a port at one end such that the plunger can push (i.e., discharge) the liquid out of the syringe pump. Syringe pumps can be coupled to an actuator that mechanically drives the plunger to control the delivery of liquid to the patient.

Syringe pumps may also be used to deliver various drugs including analgesics, antiemetics, or other fluids. The medication may be administered via an intravenous liquid line very quickly (e.g., in a bolus) or over a length of time. Syringe pumps may also be used in non-medical applications, such as in microreactors, testing, and/or in chemical processing applications.

SUMMARY

In one aspect of the present disclosure, a pump includes a reservoir, a port, a plunger, and a reference-volume assembly. The reservoir is configured to deliver a liquid. The port is coupled to the reservoir and is configured to discharge the liquid. The plunger includes a piston coupled to a shaft. The piston is disposed within the reservoir in sliding engagement with an inner surface of the reservoir. The piston defines a liquid side of the reservoir and a non-liquid side of the reservoir whereby movement of the plunger towards the liquid side of the reservoir discharges liquid through the port. The reference-volume assembly is coupled to the reservoir at an opposite end of the reservoir relative to the port. The reference-volume assembly includes a reference-volume chamber, a speaker, and a reference microphone. The reference-volume chamber is in acoustic communication with the non-liquid side of the reservoir. The speaker is disposed within the reference-volume chamber, and the reference microphone is disposed within the reference-volume chamber. A variable-volume microphone may be disposed within the reservoir to sense the sound wave within the reservoir and/or disposed on the reference-volume assembly to sense the sound wave within the reservoir.

In another aspect of the present disclosure, a system may include a pump (as described above), an actuator, a linear position sensor, and a processor. The actuator is coupled to the shaft of the pump to actuate the pump and the linear position sensor is coupled to the shaft to sense a position of the shaft. The processor is coupled to the actuator and the linear position sensor to estimate a volume of discharged liquid as a function of the position of the shaft.

In another aspect, a system may include a pump (as described above), a variable-volume microphone, and a processor. The variable-volume microphone senses the sound wave within the non-liquid side of the reservoir. The processor is operatively coupled to the speaker, and the reference and variable-volume microphones to instruct the speaker to generate a plurality of acoustic frequencies and estimate a volume of discharged liquid as a function of the acoustic feedback from the variable-volume and reference microphones.

In yet another aspect of the present disclosure, a pump includes a reservoir, a port, a plunger, an additional reservoir, an additional port, an additional plunger, and a reference-volume assembly. The reservoir is configured to deliver a liquid. The port is coupled to the reservoir and is configured to discharge the liquid. The plunger includes a piston coupled to a shaft. The piston is disposed within the reservoir in sliding engagement with an inner surface of the reservoir. The piston defines a liquid side of the reservoir and a non-liquid side of the reservoir whereby movement of the plunger towards the liquid side of the reservoir discharges liquid through the port.

The additional reservoir is configured to deliver an additional liquid. The additional port is coupled to the additional reservoir and is configured to discharge the additional liquid. The additional plunger includes an additional piston coupled to the additional shaft. The additional piston is disposed within the additional reservoir in sliding engagement with an inner surface of the additional reservoir. The additional piston defines a liquid side of the additional reservoir and a non-liquid side of the additional reservoir whereby movement of the additional plunger towards the liquid side of the additional reservoir discharges liquid through the additional port.

The reference-volume assembly is coupled to the reservoir at an opposite end of the reservoir relative to the port, and the reference-volume assembly is further coupled to the additional reservoir at an opposite end of the additional reservoir relative to the additional port. The reference-volume assembly includes a reference-volume chamber, a speaker, and a reference microphone. The reference-volume chamber is in acoustic communication with the non-liquid side of the reservoir, and the reference-volume chamber is further in acoustic communication with the non-liquid side of the additional reservoir. The speaker is disposed within the reference-volume chamber, and the reference microphone disposed within the reference-volume chamber. Optionally, one or more of the first and second reservoirs are attachable to the reference-volume assembly.

In another aspect of the present disclosure, the pump includes a manifold. The manifold includes first and second connector ports, a discharge port, and a liquid path. The first connector port is coupled to the port, and the second connector port is coupled to the additional port. The liquid path fluidly connects together the first and second connector ports to the discharge port. The manifold is optionally attachable to the first and second connector ports.

In another aspect of the present disclosure, the pump includes a variable-volume microphone disposed within the reservoir or on the reference-volume assembly and is configured to sense the sound wave within the reservoir. The pump may also include an additional variable-volume microphone disposed within the additional reservoir of on the reference-volume assembly and configured to sense the sound wave within the additional reservoir.

In another aspect of the present disclosure, a system for estimating liquid deliver includes a pump as described above, a variable-volume microphone, and a processor. The variable-volume microphone senses the sound wave within the non-liquid side of the reservoir. The processor is operatively coupled to the speaker, and the reference and variable-volume microphones. The processor is configured to instruct the speaker to generate a plurality of acoustic frequencies and to estimate a volume of discharged liquid as a function of the acoustic feedback from the variable-volume and reference microphones.

In yet another aspect of the present disclosure, a pump includes an acoustic housing, a reservoir, a port, a plunger, and a reference-volume assembly. The reservoir is configured to deliver a liquid and is disposed within the acoustic housing. The port is coupled to the reservoir and is configured to discharge the liquid. The plunger has a piston coupled to a shaft. The plunger is disposed within the acoustic housing, and the piston is disposed within the reservoir in sliding engagement with an inner surface of the reservoir. The piston defines a liquid side of the reservoir and a non-liquid side of the reservoir whereby movement of the plunger towards the liquid side of the reservoir discharges liquid through the port. The reference-volume assembly is coupled to the acoustic housing through an acoustic port. The reference-volume assembly includes a reference-volume chamber, a speaker, and a reference microphone. The reference-volume chamber is in acoustic communication with the acoustic housing via the acoustic port. The speaker is disposed within the reference-volume chamber, and the reference microphone is disposed within the reference-volume chamber. The pump may also include an actuator coupled to the shaft to actuate the plunger, and the actuator may be disposed within the acoustic housing.

The pump may also include an additional reservoir, an additional port, and an additional plunger. The additional reservoir is configured to deliver an additional liquid, and the additional reservoir is disposed within the acoustic housing. The additional port is coupled to the additional reservoir and is configured to discharge the additional liquid. The additional plunger has an additional piston coupled to the additional shaft. The additional plunger is disposed within the acoustic housing, and the additional piston is disposed within the additional reservoir in sliding engagement with an inner surface of the additional reservoir. The additional piston defines a liquid side of the additional reservoir and a non-liquid side of the additional reservoir whereby movement of the additional plunger towards the liquid side of the additional reservoir discharges liquid through the additional port.

The pump may also include a manifold. The manifold includes first and second connector ports, a discharge port, and a liquid path. The first connector port is coupled to the port, and the second connector port is coupled to the additional port. The liquid path fluidly connects together the first and second connector ports to the discharge port. The manifold is optionally attachable to the first and second connector ports.

In yet an additional aspect of the present disclosure, a system for estimating liquid delivery includes a pump as described above, an actuator, a linear position sensor, and a processor. The actuator is coupled to the shaft. The linear position sensor is coupled to the shaft and is configured to sense a position of the shaft. The processor is operatively coupled to the actuator and the linear position sensor to estimate a volume of discharged liquid as a function of the position of the shaft, e.g., as determined by the linear position sensor.

In another aspect of the present disclosure, a system for estimating liquid delivery includes a pump as described above, a variable-volume microphone, and a processor. The variable-volume microphone senses the sound wave within the non-liquid side of the reservoir. The processor is operatively coupled to the speaker, and the reference and variable-volume microphones. The processor is configured to instruct the speaker to generate a plurality of acoustic frequencies and estimate a volume of discharged liquid as a function of the acoustic feedback from the variable-volume and reference microphones.

In yet another aspect of the present disclosure, a pump includes an acoustic housing, an additional acoustic housing, a reservoir, a port, a plunger, an additional reservoir, an additional port, an additional plunger, and an a reference-volume assembly. The reservoir is configured to deliver a liquid and is disposed within the acoustic housing. The port is coupled to the reservoir and is configured to discharge the liquid. The plunger has a piston coupled to a shaft. The plunger is disposed within the acoustic housing. The piston is disposed within the reservoir and is in sliding engagement with an inner surface of the reservoir, and the piston defines a liquid side of the reservoir and a non-liquid side of the reservoir whereby movement of the plunger towards the liquid side of the reservoir discharges liquid through the port. The additional reservoir is configured to deliver an additional liquid. The additional reservoir is disposed within the additional acoustic housing. The additional port is coupled to the additional reservoir and is configured to discharge the additional liquid. The additional plunger has an additional piston coupled to the additional shaft. The additional plunger is disposed within the additional acoustic housing. The additional piston is disposed within the additional reservoir in sliding engagement with an inner surface of the additional reservoir. The additional piston defines a liquid side of the additional reservoir and a non-liquid side of the additional reservoir whereby movement of the additional plunger towards the liquid side of the additional reservoir discharges liquid through the additional port.

The reference volume assembly is coupled to the acoustic housing through an acoustic port and is coupled to the additional acoustic housing through an additional acoustic port. The reference-volume assembly includes a reference-volume chamber, a speaker, and a reference microphone. The reference-volume chamber is in acoustic communication with the acoustic housing via the acoustic port. The reference-volume chamber is in acoustic communication with the additional acoustic housing via the additional acoustic port. The speaker is disposed within the reference-volume chamber. The reference microphone is disposed within the reference-volume chamber.

The pump may also include an actuator coupled to the shaft to actuate the plunger. The actuator may be disposed within the acoustic housing. The pump may include an additional actuator coupled to the additional shaft to actuate the additional plunger.

The pump may also include a manifold. The manifold includes first and second connector ports, a discharge port, and a liquid path. The first connector port is coupled to the port, and the second connector port is coupled to the additional port. The liquid path fluidly connects together the first and second connector ports to the discharge port. The manifold is optionally attachable to the first and second connector ports.

In yet an additional aspect of the present disclosure, a system for estimating liquid delivery includes a pump as described above, an actuator, a linear position sensor, and a processor. The actuator is coupled to the shaft. The linear position sensor is coupled to the shaft and is configured to sense a position of the shaft. The processor is operatively coupled to the actuator and the linear position sensor and is configured to estimate a volume of discharged liquid as a function of the position of the shaft.

In yet another aspect thereof, a system for estimating liquid delivery includes the pump as described above, a variable-volume microphone, and a processor. The variable-volume microphone senses the sound wave within the non-liquid side of the reservoir. The processor is operatively coupled to the speaker, and the reference and variable-volume microphones. The processor is configured to instruct the speaker to generate a plurality of acoustic frequencies and estimate a volume of discharged liquid as a function of the acoustic feedback from the variable-volume and reference microphones.

In yet an additional aspect of the present disclosure, a pump includes a reservoir, a port, a plunger, and a linear position sensor. The reservoir is configured to deliver a liquid. The port is coupled to the reservoir and is configured to discharge the liquid. The plunger has a piston coupled to a shaft. The piston is disposed within the reservoir in sliding engagement with an inner surface of the reservoir. The piston defines a liquid side of the reservoir and a non-liquid side of the reservoir whereby movement of the plunger towards the liquid side of the reservoir discharges liquid through the port. The linear position sensor is configured to sense a position of the shaft.

The pump may also include a housing such that the reservoir is disposed within the housing, and the plunger is disposed within the housing. The pump may also include an actuator coupled to the shaft to actuate the plunger and disposed within the housing. The linear position sensor may also be disposed within the housing.

The pump may further comprise an additional reservoir, an additional port, an additional plunger, and an additional linear position sensor. The additional reservoir is configured to deliver an additional liquid. The additional port is coupled to the additional reservoir and is configured to discharge the additional liquid. The additional plunger has an additional piston coupled to the additional shaft. The additional piston is disposed within the additional reservoir in sliding engagement with an inner surface of the additional reservoir. The additional piston defines a liquid side of the additional reservoir and a non-liquid side of the additional reservoir whereby movement of the additional plunger towards the liquid side of the additional reservoir discharges liquid through the additional port. The additional linear position sensor is configured to sense a position of the additional shaft.

The pump may also include a manifold. The manifold includes first and second connector ports, a discharge port, and a liquid path. The first connector port is coupled to the port, and the second connector port is coupled to the additional port. The liquid path fluidly connects together the first and second connector ports to the discharge port. The manifold is optionally attachable to the first and second connector ports.

The pump may also include a housing such that the reservoir and the additional reservoir are disposed within the housing, and the plunger and the additional plunger are also disposed within the housing.

The pump may also include an actuator coupled to the shaft to actuate the plunger, and an additional actuator coupled to the additional shaft to actuate the additional plunger. The actuator and the additional actuator may be disposed within the housing. The linear position sensor and/or the additional linear position sensor may be a capacitive sensor coupled to the shaft or a linear optical position sensor. The linear position sensor and/or the additional linear position sensor may be disposed within the housing.

In some aspects of the present disclosure, the linear position sensor includes an optical target and an optical ranging assembly. The optical target is coupled to the shaft. The optical ranging assembly is configured to determine a range of the optical target thereby estimating a linear position of the shaft.

The optical target may be a reflective target, and the optical ranging assembly may include an illuminator configured to illuminate the reflective target thereby determining the linear position of the shaft from a reflection of the illumination of the reflective target.

The optical target may be a light source, and the optical ranging assembly may be configured to determine the linear position of the shaft from a measured intensity of the light source measured by the optical ranging assembly.

In another aspect of the present disclosure, a system for estimating liquid delivery includes a pump, an actuator, and a processor. The actuator is coupled to the shaft, and the processor is operatively coupled to the actuator and the linear position sensor to estimate a volume of discharged liquid as a function of the position of the shaft.

In yet another aspect of the present disclosure, one or more of the herein described pumps may include one or more optional features as described below. One or more of the pistons of a pump as described herein may comprise a seal disposed along a periphery of the piston. The reservoir may be cylindrically shaped thereby defining a circular cross section; the piston can engage an inner surface of the reservoir along the circular cross section. The reservoir may be cuboid shaped thereby defining a rectangular cross section, and the piston can engage the inner surface of the reservoir along the rectangular cross section.

The pump may include a vent in fluid communication with the non-liquid side of the reservoir. The vent may be further configured to acoustically seal the non-liquid side of the reservoir from outside the reservoir.

A pump as described herein may include a one-way valve in fluid communication with the non-liquid side of the reservoir. The one-way valve may be configured to allow gas to enter into the non-liquid side of the reservoir from outside the reservoir.

One or more of the pumps described herein may include a plunger that is moveable between a fully discharged position and a fully loaded position such that the reference-volume chamber is in fluid communication with the non-liquid side of the reservoir when the plunger is positioned anywhere between the fully discharged position and the fully loaded position.

A pump as described herein may include a reference-volume chamber that further includes a conduit configured to receive the shaft. The shaft may be in sliding engagement with the conduit. The conduit may further comprise a seal configured to receive the shaft and acoustically seal the non-liquid side of the reservoir as the shaft engages with the conduit. The reference-volume assembly may further comprise an acoustic port in acoustic communication with the reference-volume chamber and the non-liquid side of the reservoir.

A pump as described herein may include a variable-volume microphone. The non-liquid side of the reservoir may be configured to receive the variable-volume microphone for attachment to the inner surface of the reservoir. The variable-volume microphone is configured to sense the sound wave within the non-liquid side of the reservoir. Additionally or alternatively, the variable-volume microphone may be attached to the reference-volume assembly to sense the sound wave within the non-liquid side of the reservoir.

The actuator described herein may be a linear actuator, a screw-type linear actuator, a linear track actuator, a linear servo, a linear stepper motor, a linear motor, or some other actuator.

In yet an additional aspect of the present disclosure, a method for estimating liquid delivery includes one or more acts, such as: (1) positioning a plunger of a pump in a first position; (2) generating a sound wave; (3) applying the sound wave to a reference chamber; (4) communicating the sound wave to a non-liquid side of a reservoir of the pump; (5) sensing the sound wave in the reference chamber; (6) sensing the sound wave in the non-liquid side of the reservoir of the pump; (7) comparing the sensed sound wave in the reference chamber to the sensed sound wave in the non-liquid side of the reservoir to determine a first volume of liquid within the liquid side of the reservoir; (8) actuating the plunger of the pump to a second position; (9) comparing the sensed sound wave in the reference chamber to the sensed sound wave in the non-liquid side of the reservoir to determine a second volume of liquid within the liquid side of the reservoir; and/or (10) comparing the first volume to the second volume to determine an amount of liquid discharged.

In yet another aspect of the present disclosure, a system for preparing a syringe pump includes a monitoring client, a pharmacy computer, a compounding robot, a syringe pump, and a data download device. The syringe pump may be any disclosed above or herein. The monitoring client is configured to communicate a prescription order via a user interface. The pharmacy computer is in operative communication with the monitoring client to receive the prescription order. The compounding robot is configured to prepare the prescription into at least one liquid corresponding to the prescription order. The syringe pump is configured to receive the at least one liquid corresponding to the prescription order. The data download device is configured to download the prescription order into a memory of the pill dispenser. The syringe pump includes a reference volume attached thereto. The compounding robot may fill the syringe pump with the at least one liquid. The compounding robot may be in operative communication with the data download device. The compounding robot may instruct the data download device to download the prescription order into the memory of the pill dispenser. The data download device may receive the prescription order from the compounding robot and/or the pharmacy computer.

BRIEF DESCRIPTION OF THE DRAWINGS

These and other aspects will become more apparent from the following detailed description of the various embodiments of the present disclosure with reference to the drawings wherein.

DETAILED DESCRIPTION

Figure 1:
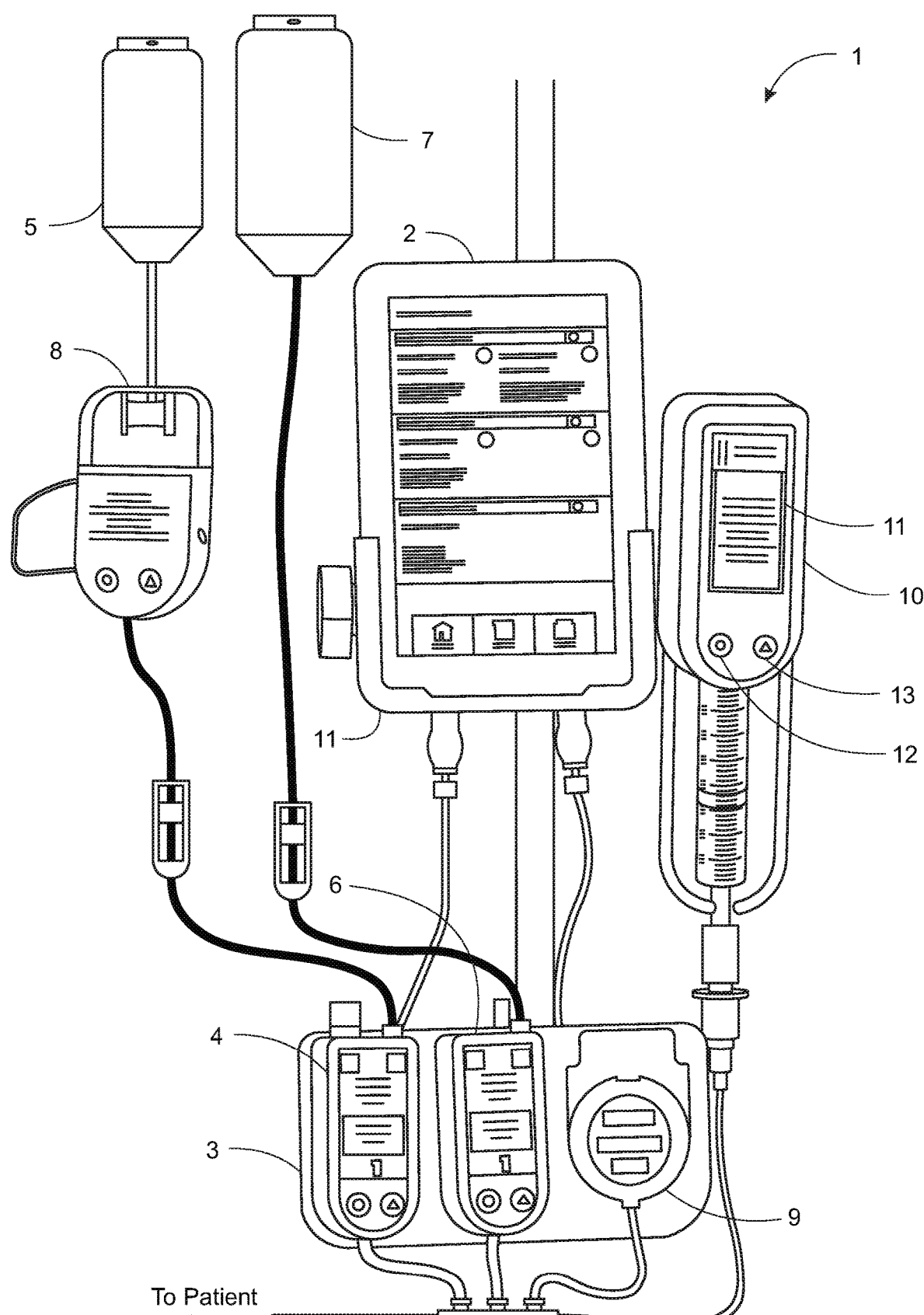
FIG. 1 is a illustration of an electronic patient-care system having a syringe pump in accordance with an embodiment of the present disclosure.

FIG. 1 shows an exemplary arrangement of a system 1 for electronic patient care in accordance with an embodiment of the present disclosure. The system 1 includes a monitoring client 2 that is linked to a number of patient-care devices via docks 3 and 11, including an infusion pump 4 connected to and delivering from a smaller bag of liquid 5, an infusion pump 6 connected to and delivering from a larger bag of liquid 7, a drip detection device 8 connected to tubing from the smaller bag 5, and a microinfusion pump 9. System 1 also includes a syringe pump 10 connected wirelessly to the monitoring client 2. In some embodiments, the monitoring client 2 may communicate with these patient-care devices in a wired fashion, as shown in FIG. 1 for the infusion pumps 4 and 6, and the microinfusion pump 9 (via docks 3 and 11). Additionally or alternatively, the monitoring client 2 may communicate wirelessly with patient-care devices, as suggested by the absence of a wired connection between the syringe pump 10 and the monitoring client 2.

In some embodiments, a wired connection between the monitoring client 2 and a patient-care device also affords an opportunity for electrical power to be supplied to the patient-care device from the monitoring client 2. In this exemplary embodiment, the monitoring client 2 may include the electronic circuitry necessary to convert the voltage to power the patient-care device from either a battery attached to the monitoring client 2 or from an Alternative Current ("AC") line voltage fed into the monitoring client 2 from a power outlet (not shown) in a patient's room. Additionally or alternatively, the dock 3 supplies power to the infusion pumps 4 and 6, and to the microinfusion pump 9, e.g., from a signal generated from an AC line voltage.

In an embodiment, the monitoring client 2 is capable of receiving information about each patient-care device with which it is linked either directly from the device itself, or via a docking station, such as, for example, the dock 3 onto which the patient-care device may be mounted. The dock 3 may be configured to receive one or more patient-care devices via a standardized connection mount, or in some cases via a connection mount individualized for the particular device. For example, infusion pumps 4 and 6 may be mounted to the dock 3 via a similar connection mount, whereas the microinfusion pump 9, for example, may be mounted to the dock 3 via a connection mount configured for the particular dimensions of the microinfusion pump's 9 housing.

The dock 3 may be configured to electronically identify the particular patient-care device being mounted on the docking station, and to transmit this identifying information to the monitoring client 2, either wirelessly or via a wired connection. Additionally or alternatively, wireless patient-care devices may transmit the identifying information wirelessly to the monitoring client 2, e.g., during a discovery protocol. Additionally, the particular patient-care device may be preprogrammed with treatment information (e.g., patient-treatment parameters such as an infusion rate for a predetermined infusion liquid) that is transmitted to the monitoring client 2. For example, the syringe pump 10 may include identity information and treatment information, such as what medication has been prescribed to the patient, what liquid is within the syringe pump's 10 reservoir, how much and how long the liquid is prescribed to be delivered to the patient, who are the authorized caregivers, etc. In some embodiments of the present disclosure, the monitoring client 2 communicates with EMR records to verify that the preprogrammed treatment information is safe for an identified patient and/or the preprogrammed treatment information matches the prescribed treatment stored in the EMR records.

In some embodiments, the drip detection device 8 may communicate with the monitoring client 2 either wirelessly or in a wired connection. If an aberrant liquid flow condition is detected (e.g., because the tubing to the patient has become occluded), a signal may be transmitted to monitoring client 2, which (1) may display the flow rate of liquid from the liquid container 5 in a user interface either locally on the monitoring client 2, or more remotely to a user interface at a nurse's station or a handheld communications device, (2) may trigger an auditory or visual alarm, and/or (3) may cause the monitoring client 2 to alter the rate of infusion of a pump 4 connected to a bag 5, by either terminating the infusion or otherwise changing the pumping rate The aberrant liquid flow condition may also cause an audible alarm (and/or vibration alarm) on the infusion pump 4 or the drip detection device 8, or cause the infusion pump 4 to modify or stop the pumping, e.g., when the aberrant liquid flow condition exceed predefined ranges of operation.

The alarms may occur simultaneously on several devices or may follow a predetermined schedule. For example, when an occlusion occurs in a line connected to the infusion pump 4, (1) the drip detection device 8 alarms using its internal speaker and an internal vibration motor, (2) thereafter, the infusion pump 4 alarms using its internal speaker and an internal vibration motor, (3) next, the monitoring client 2 alarms using its internal speaker and an internal vibration motor, and (4) finally, a remote communicator (e.g., a smart phone, blackberry-based phone, Android-based phone, iphone, etc.) alarms using its internal speaker and an internal vibration motor. In some embodiments, the syringe pump 10 may be connected to the drip detection device 8 and detect aberrant liquid flow conditions as described above.

In some embodiments, the syringe pump 10 may be programmable to allow for continued operation at a predetermined pumping rate should communications fail between the monitoring client 2 and the syringe pump 10, either because of a malfunction in the monitoring client 2, in the communications channel between the monitoring client 2 and the syringe pump 10, or in the syringe pump 10 itself. In some embodiments, this independent function option is enabled when the medication being infused is pre-designated for not being suspended or held in the event of a malfunction in other parts of the system. In some embodiments, the syringe pump 10 is programmed to operate independently in a fail safe mode and may also be configured to receive information from a drip detection device 8 directly, rather than through a monitoring client 2 (e.g., in embodiment where the drip detection device 8 is used in conjunction with the syringe pump 10); with this option, the syringe pump 10 may be programmed, in some embodiments, to stop an infusion if the drip detection device 8 detects an aberrant flow condition (such as, e.g., a free-flow condition or an air bubble present in the infusion line). In some embodiments, one or more of the pumps 4, 6, and 10 may have internal liquid flow meters and/or can operate independently as a stand-alone device. Additionally or alternatively, an internal liquid flow meter of the syringe pump 10 may be independently determined by a flow meter of the drip detection device 8 by the monitoring client 2, in embodiments where the devices 8 and 10 are used together.

The monitoring client 2 may also remotely send a prescription to a pharmacy. The prescription may be a prescription for infusing a fluid using the syringe pump 10. The pharmacy may include one or more computers connected to a network, e.g., the internet, to receive the prescription and queue the prescription within the one or more computers. The pharmacy may use the prescription to compound the drug (e.g., using an automated compounding device coupled to the one or more computers or manually by a pharmacists viewing the queue of the one or more computers), pre-fill a fluid reservoir or cartridge of a syringe pump 10, and/or program the syringe pump 10 (e.g., a treatment regime is programmed into the syringe pump 10) at the pharmacy in accordance with the prescription. The reservoir or cartridge may be automatically filled by the automated compounding device and/or the syringe pump 10 may be automatically programmed by the automated compounding device. The automated compounding device may generate a barcode, RFID tag and/or data. The information within the barcode, RFID tag, and/or data may include the treatment regime, prescription, and/or patient information. The automated compounding device may: attach the barcode to the syringe pump 10 or to the reservoir, cartridge, or disposable portion of the syringe pump 10; attach the RFID tag to the syringe pump 10 or the reservoir, cartridge, or disposable portion of the syringe pump 10; and/or program the RFID tag or memory within the syringe pump 10 or the reservoir, cartridge, or disposable portion of the syringe pump 10 with the information or data. The data or information may be sent to a database that associates the prescription with the syringe pump 10 or the reservoir, cartridge, or disposable portion of the syringe pump 10, e.g., using a serial number or other identifying information within the barcode, RFID tag, or memory.

The syringe pump 10 may have a scanner, e.g., an RFID interrogator that interrogates a reservoir, disposable portion, or cartridge of the syringe pump 10 to determine that it is the correct fluid within the fluid reservoir or it is the correct fluid reservoir, disposable portion or cartridge, the treatment programmed into the syringe pump 10 corresponds to the fluid within the fluid reservoir, disposable portion or cartridge, and/or the syringe pump 10 and reservoir, disposable portion or cartridge of the syringe pump 10 are correct for the particular patient (e.g., as determined from a patient's barcode, RFID, or other patient identification). For example, a serial number of a reservoir, disposable portion as scanned by the syringe pump 10 is compared to a serial number in electronic medical records to determine if it correctly corresponds to a patient's serial number within the electronic medical records; the syringe pump 10 may scan a RFID tag or barcode of a patient to obtain a serial number of a patient which is also compared to the patient's serial number within the electronic medical records (e.g., the serial number of a reservoir, disposable portion, or cartridge of the syringe pump 10 or a serial number stored within memory of the syringe pump 10 should be associated with the patient's serial number as scanned within the electronic medical records). The syringe pump 10 may issue an error or alarm if the serial numbers do not match, in some specific embodiments. Additionally or alternatively, the monitoring client 6 may scan the reservoir, disposable portion, cartridge, or syringe pump 10 to determine that it is the correct fluid within the fluid reservoir, it is the correct fluid reservoir, the treatment programmed into the syringe pump 10 corresponds to the fluid within the fluid reservoir or cartridge, and/or the fluid reservoir and syringe pump 10 are correct for the particular patient (e.g., as determined from a patient's barcode, RFID, or other patient identification). Additionally or alternatively, the monitoring client 6 or syringe pump 10 may interrogate an electronic medical records database and/or the pharmacy to verify the prescription or download the prescription, e.g., using a barcode serial number on the syringe pump 10, or a reservoir, cartridge, or disposable portion of the syringe pump 10.

The liquid being delivered to a patient may be monitored by the monitoring client 2 to determine if all the medications being delivered are safe for the patient. For example, the monitoring client 2 may log the medication delivered from the syringe pump 10 as communicated by the syringe pump 10 to the monitoring client 2, and the monitoring client 2 may also log the medication being delivered by the infusion pumps 4 and 6, and/or the microinfusion pump 9. The monitoring client 1 may make a determination from the logged data to determine if the aggregate amounts and types of medication being delivered are safe. For example, the monitoring client 2 may determine if the IV bag 5 is contraindicated with the medication in the syringe pump 10. Additionally or alternatively, in some embodiments, the monitoring client 2 may monitor the delivery of the liquid in the IV bag 8 and one or more boluses delivered by the syringe pump 10 to determine if the total dose exceeds a predetermined threshold, e.g., the medication in the IV bag 5 and syringe pump 10 may be the same type or class of drug, and the monitoring client 2 may determine if the drugs are safe when combined as delivered to the patient. The syringe pump 10 may also communicate with the infusion pumps 4 and 6, and/or the microinfusion pump 9 to make the same determination; In this exemplary embodiment, the syringe pump 10 may communicate with the devices directly (via wirelessly or wired communications) or through the monitoring client 2 (via wirelessly or wired communications). In some embodiments of the present disclosures, one or more communication modules (e.g., each having the capabilities to communicate via one or more protocols) may be connected to the syringe pump 10 and/or may be connected together and then connected to the syringe pump 10 to enable the syringe pump 10 to communicate via the communication modules.

The syringe pump 10 includes a touch screen interface 11 (which may be detachable), a start button 12, and a stop button 13. The user interface 11 may be used to program treatment regimes, such as flow rates, bolus amounts, or other treatment parameters. After a treatment regime is programmed into the syringe pump 10, the syringe pump 10 may query a database (e.g., Electronic Medical Records ("EMR"), Drug Error Reduction System ("DERS"), or other database) to determine if the treatment regime is safe for the particular patient or for any patient. For example, the syringe pump 10 may query the EMR database (e.g., via a wireless link, wired link, WiFi, cell-phone network, or other communications technology) to determine if the treatment regime from the syringe pump 10 is safe based upon patient information stored (e.g., age, weight, allergies, condition, etc.) in the EMR records. Additionally or alternatively, the syringe pump 10 may query the DERS database (e.g., via a wireless link, wired link, WiFi, cell-phone network, or other communications technology) to determine if the treatment regime from the syringe pump 10 is safe based upon predetermined safety criteria in the DERS records In some embodiments, if the treatment regime is determined to be safe, a prompt may request user confirmation of the treatment regime. After user confirmation, the user (e.g., caregiver, nurse, or other authorized person) may press the start button 12. In some embodiments, the stop button 13 may be pressed at any time to stop treatment.

In some embodiments, if the EMR and/or DERS determines that the treatment regime exceeds a first set of criteria, treatment may continue if the user confirms the treatment (e.g., with an additional warning, user pass code, and/or additional authentication or authorization, etc.); in this embodiment, the EMR or DERS may prevent the treatment from being delivered if the EMR and/or DERS determines that the treatment regime exceeds a second set of criteria, e.g., the treatment is not safe under any circumstances for any patient, for example.

Figure 2:
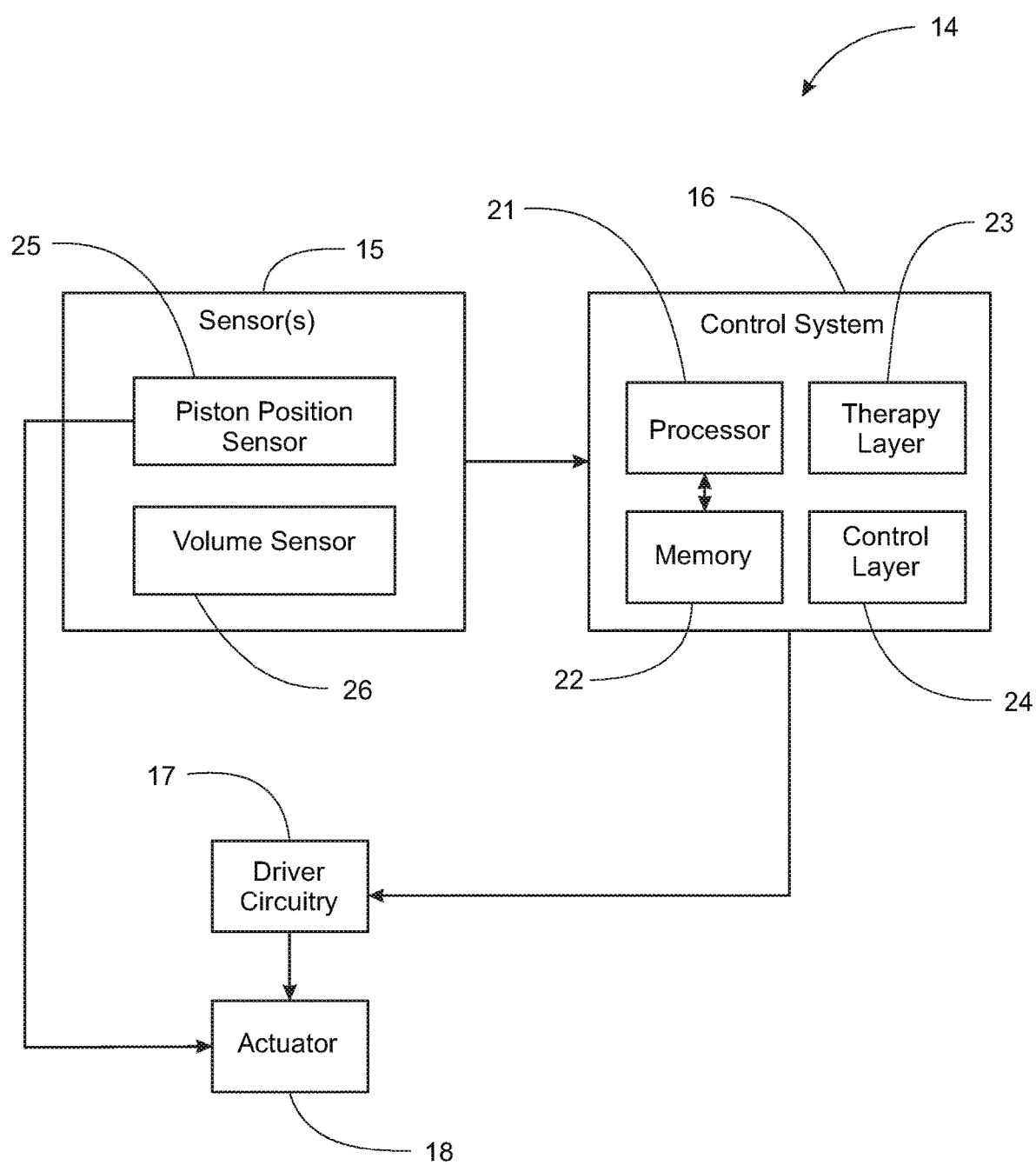
FIG. 2 is a block diagram of a system for controlling a syringe pump in accordance with an embodiment of the present disclosure.

FIG. 2 is a block diagram of a system 14 for controlling a syringe pump in accordance with an embodiment of the present disclosure. The system 14 of FIG. 2 may be used to control the syringe pump 10 of FIG. 1, or the syringe pumps of FIGS. 3-10 described below.

The system 14 includes one or more sensors 15, a control system 16, driver circuitry 17, and an actuator 18. The system 14 operates to control a position of a plunger within a syringe pump using the actuator 18. The processor 21 may control the actuator 18 to actuate any plunger described herein. For example, the actuator 18 may be coupled to the shaft 19 of FIG. 3 (described below) to control the position of the plunger 20.

The control system 16 includes a processor 21 coupled to a memory 22. The processor 21 and memory 22 may be coupled together through a serial connection, a parallel connection, a memory bus, or other data communications link. The processor 21 may include one or more cores, may use any instruction set, and/or may use any instruction set architecture or microarchitecture. For example, the processor 21 may have the Von Neumann architecture, the Harvard architecture, may be a microcontroller, may use a MIPS instruction set, a RISC instruction set, and/or a CISC instruction set, etc.

The control system 16 includes a therapy layer 23 and a control layer 24. The therapy layer 23 may instruct the control layer 24 when and how much liquid to discharge from a syringe pump 10. For example, the therapy layer 23 may instruct the control layer 24 to discharge 10 millimeters of liquid per minutes, etc. The therapy layer 23 may also control the stop time and start time of liquid delivery to the patient. For example, the therapy layer 23 may include a liquid deliver rate profile based upon time. The therapy layer 23 may command a liquid discharge rate to the control layer 24 as the values within the liquid deliver rate profile indicate that it is time to change the delivery rate. The control layer 24 receives a target liquid discharge rate from the therapy layer 23 and uses the target liquid discharge rate as a set point in a control loop and controls the position of the actuator 18 to achieve the set point. For example, the control layer 24 may implement a proportional-integral-derivative ("PID") control algorithm having an output to the driver circuitry 17 and feedback from the one or more sensor 15, such as the piston position sensor 25 and/or a volume sensor 26. The control layer 24, in various embodiments, may have a target discharge rate, a target volume to discharge, a target remaining liquid volume, some combination thereof, or the like.

The therapy layer 23 and control layer 24 may be implemented in hardware, software, software in execution on the processor 21, firmware, microcode, assembly, virtualization, bytecode, VHDL, Verilog, in a PAL, in a PLD, in a CPLD, the like, or some combination thereof. For example, the therapy layer 23 and/or the control layer 24 may be stored in the memory 22 as an operative set of processor 21 executable instructions configured for execution on one or more of the processors 21. The memory 22 may be volatile memory, non-volatile memory, a hard disk, magnetic storage, flash storage, EEPROM, ROM, optical-memory, other non-transitory processor readable medium, the like, or some combination thereof.

The control system 16 outputs one or more signals to the driver circuit 17 that drives the actuator 18. The driver circuitry 17 may include power MOSFETS, voltage converters, power converters, and/or additional circuitry to receive instructions from the control system 16 and apply one or more sufficient signals to the actuator 18. As the actuator 18 actuates, the sensors 15 are used by the control system 16 as feedback, including the piston position sensor 25 and/or the volume sensor 26. The piston position sensor 25 may be a linear position sensor and may be used with any position sensor described herein. The volume sensor 26 may be, in some embodiments, an acoustic volume sensing ("AVS") sensor and is used with a speaker, a reference microphone, and a variable-volume microphone (of any sufficient syringe pump described herein) to estimate the amount of liquid discharged or contained within a reservoir. In some embodiments, one of the sensors 25 and 26 is used, both are used, and/or none are used.

Figure 3:
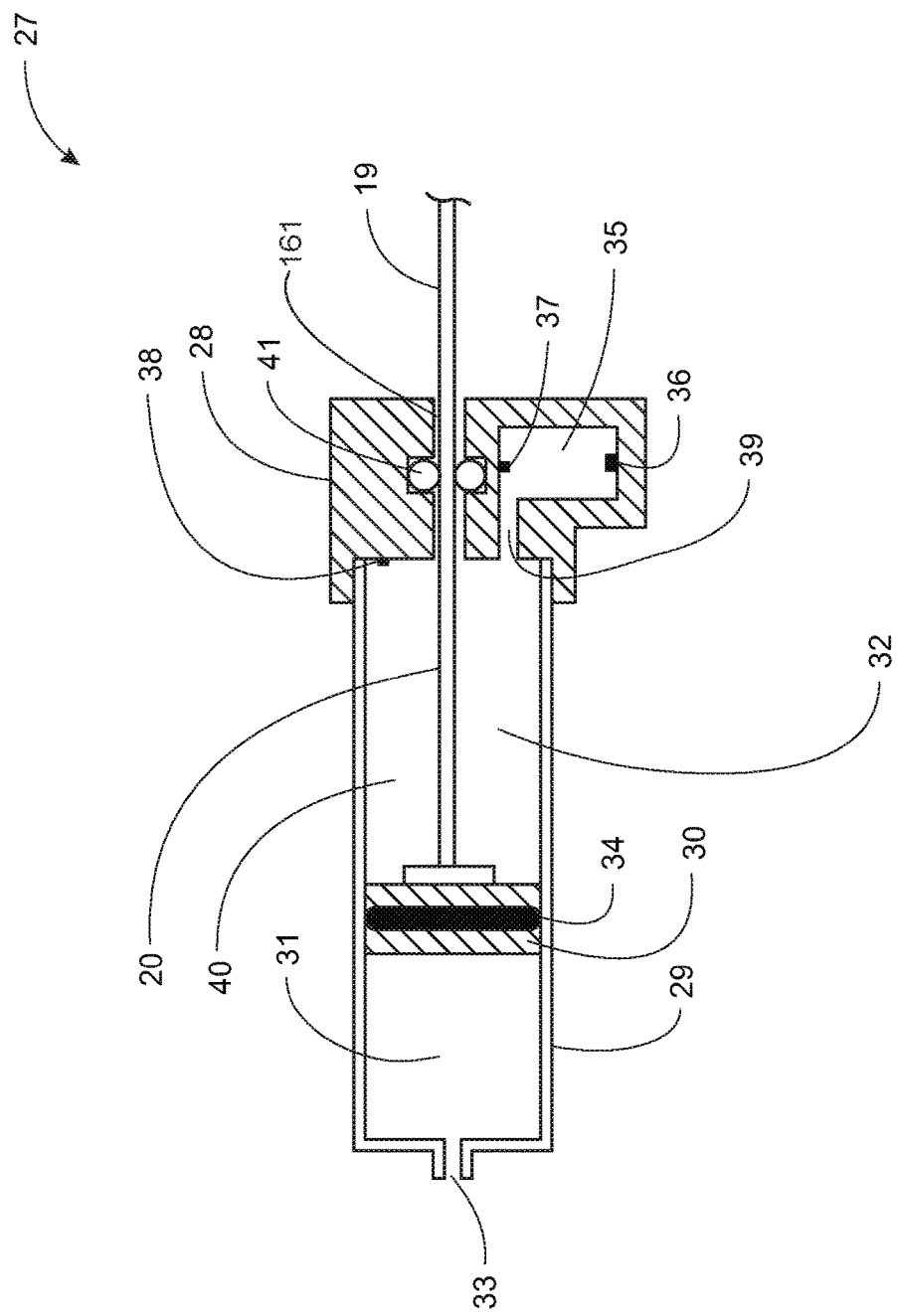
FIG. 3 shows an illustration of a syringe pump having a reference-volume assembly coupled to the reservoir of the syringe pump for acoustically estimating the amount of liquid discharged by the syringe pump in accordance with an embodiment of the present disclosure.

FIG. 3 shows an illustration of a syringe pump 27 having a reference-volume assembly 28 coupled to the reservoir 29 of the syringe pump 27 for acoustically estimating the amount of liquid discharged by the syringe pump 27 in accordance with an embodiment of the present disclosure. The syringe pump 27 may use acoustic volume sensing ("AVS") to estimate the volume of liquid within the liquid side 31 of the reservoir 29 and/or to estimate the liquid discharged from the liquid side 32 of the reservoir 29 using a speaker 6, a reference microphone 37, and a variable-volume microphone 38.

The syringe pump includes a reservoir 29 and a plunger 20. The plunger includes a shaft 19 and a piston 30 in sliding engagement with the inner surface of the reservoir 29. The shaft 19 passes through the reference-volume assembly 28 and through a seal 41. The piston 30 defines a liquid side 31 and a non-liquid side 32. As the piston 30 moves towards a port 33, the liquid is discharged through the port 33. The piston 30 may include one of more seals 34 disposed along a periphery of the piston 30 to provide a sufficient fluid seal between the liquid side 31 and the non-liquid side 32 of the reservoir 29. The port 33 may be coupled to a needle, tube, manifold, and/or may include a connector, such as screw-type threads formed thereon.

The reference volume assembly 28 includes a reference volume 35. The reference volume 35 may have a small laser drilled hole to the ambient air to allow air to fill the reference volume 35 as the piston 30 moves. The reference volume assembly 28 also includes a speaker 36, a reference microphone 37, and a variable volume microphone 38. The speaker 36 generates the sound wave that is applied to the reference volume 35. The term "sound wave" may include waves at a human perceptible frequency, a frequency not perceptible by a human, a frequency not perceptible by a living organism, ultrasonic frequencies, acoustic frequencies, or other frequency of mechanical vibration. The sound wave travels through an acoustic port 39 into the variable volume 40. The reference microphone 37 senses the sound wave within the reference volume 35 and the variable-volume microphone 38 senses the sound wave within the variable volume 40. A processor, e.g., the processor 21 of FIG. 2, is in operative communication with the speaker 36, and the reference and variable volume microphones 37 and 38. The processor 21 instructs the speaker 36 to generate a plurality of acoustic frequencies and measures the magnitude and/or phase of the sound wave sensed by the reference microphone 37 and the variable-volume microphone 38. The acoustic response can be correlated with the volume of the variable volume 40, e.g., the resonance frequency may be correlated with the volume of the variable volume 40. The processor may subtract: (1) the volume of the variable volume 40 (as measured from the acoustic response), (2) the volume displaced by the piston 30, and (3) the volume of the shaft located within the reservoir 29 from the predetermined total volume of the reservoir 29 to estimate the volume of the liquid 31 remaining in the liquid side 31 of the reservoir 29.

The processor 21 may use the speaker 36, the reference microphone 37, and the variable-volume microphone 38 to estimate the volume of fluid during a first sweep. The processor 21 may then move the shaft 19 (via actuation by an actuator) and make a second sweep. The processor 21 may compare the two volumes to determine the amount of liquid discharged through the port 33 during the actuation of the actuator coupled to the shaft 19.

Figure 4:
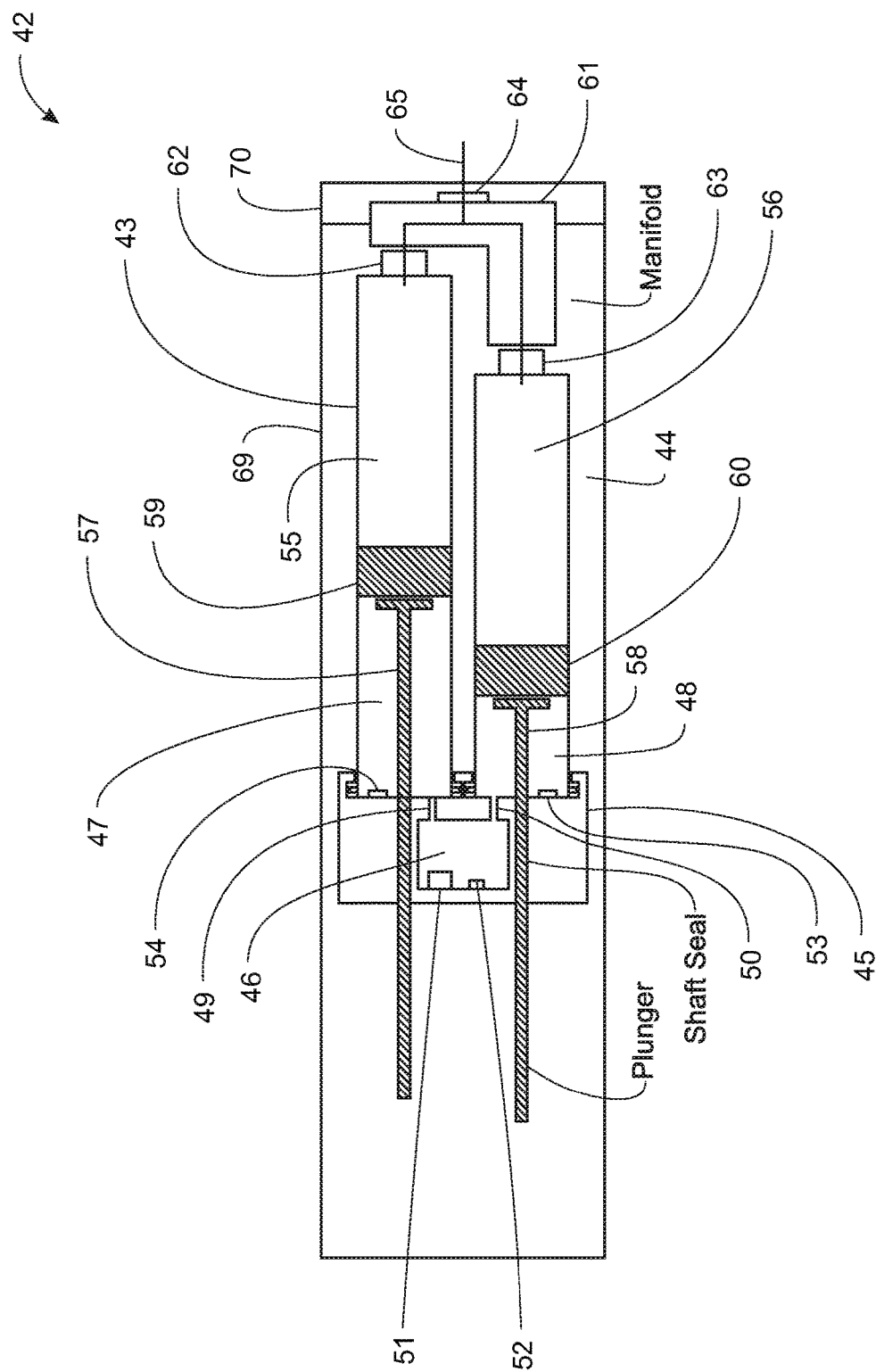
FIG. 4 shows an illustration of a syringe pump having two reservoirs and a reference-volume assembly coupled to the reservoirs for acoustically estimating the amount of liquid discharged by the syringe pump in accordance with an embodiment of the present disclosure.

FIG. 4 shows an illustration of a syringe pump 42 having two reservoirs 43 and 44, and a reference-volume assembly 45 coupled to the reservoirs 43 and 44 for acoustically estimating the amount of liquid discharged by the syringe pump 42 in accordance with an embodiment of the present disclosure. The syringe pump 42 may use acoustic volume sensing ("AVS") to estimate the volume of liquid within a liquid side 55 of a reservoir 43, the volume of liquid within a liquid side 56 of a reservoir 44, the volume of liquid discharged from the liquid side 55 of the reservoir 43, and/or the volume of liquid discharged from the liquid side 56 of the reservoir 44 using a speaker 51, a reference microphone 52, a variable-volume microphone 54, and a variable-volume microphone 53.

The syringe pump 42 includes reservoirs 43 and 44, which may be attachable and/or removable from the syringe pump 42. For example, the reservoirs 43 and 44 may be preloaded and snap into the housing 69 such that the reservoirs 43 and 44 snap into the reference-volume assembly 45. In some embodiments, the syringe pump 42 optionally includes a housing 69 and a cap 70. The housing 69 may be attachable to the cap 70, and/or the housing 69 may be attachable to other caps.

The syringe pump 42 includes a reference-volume assembly 45 having a reference-volume chamber 46 that is acoustically coupled to the non-liquid sides 47 and 48 of the two reservoirs 43 and 44, respectively. The reference-volume chamber 46 is coupled to the non-liquid side 47 of the reservoir 43 via an acoustic port 49, and the reference-volume chamber 46 is coupled to the non-liquid side 48 of the reservoir 44 via the port 50.

The reference-volume chamber 46 includes a speaker 51 and a reference microphone 52, which are both coupled to the processor 21 of FIG. 2. The reference-volume assembly 45 also includes a variable-volume microphone 53 configured to sense the sound wave within the non-liquid side 48 of the reservoir 44, and another variable volume microphone 54 configured to sense the sound wave in the non-liquid side 47 of the reservoir 43. The two variable-volume microphones 53 and 54 are coupled to the processor 21 of FIG. 2. The processor 21 may account for the volume of the shafts 57 and 58, and the volume of the pistons 59 and 60.

The syringe pump 42 also includes a manifold 61 that connects the ports 62 and 63 of the reservoirs 43 and 44, respectively, and provides a liquid path to a discharge port 64. The manifold 61 may be attachable and/or disposable. The discharge port 64 may be connected to a needle 65, a tube (not shown), a fitting (not shown), and/or may include any known connector or port. The needle 65 may be attachable and/or disposable.

The processor 21 of FIG. 2 uses the speaker 51 to generate a plurality of acoustic frequencies that are received by the reference microphone 52, and the variable-volume microphones 53 and 54. The processor 21 uses the acoustic responses of the non-liquid sides 47 and 48 to estimate their respective volumes. The two values are used by the processor 21 to estimate the volume of the liquid sides 55 and 56 of the two reservoirs 43 and 44.

Figure 5:
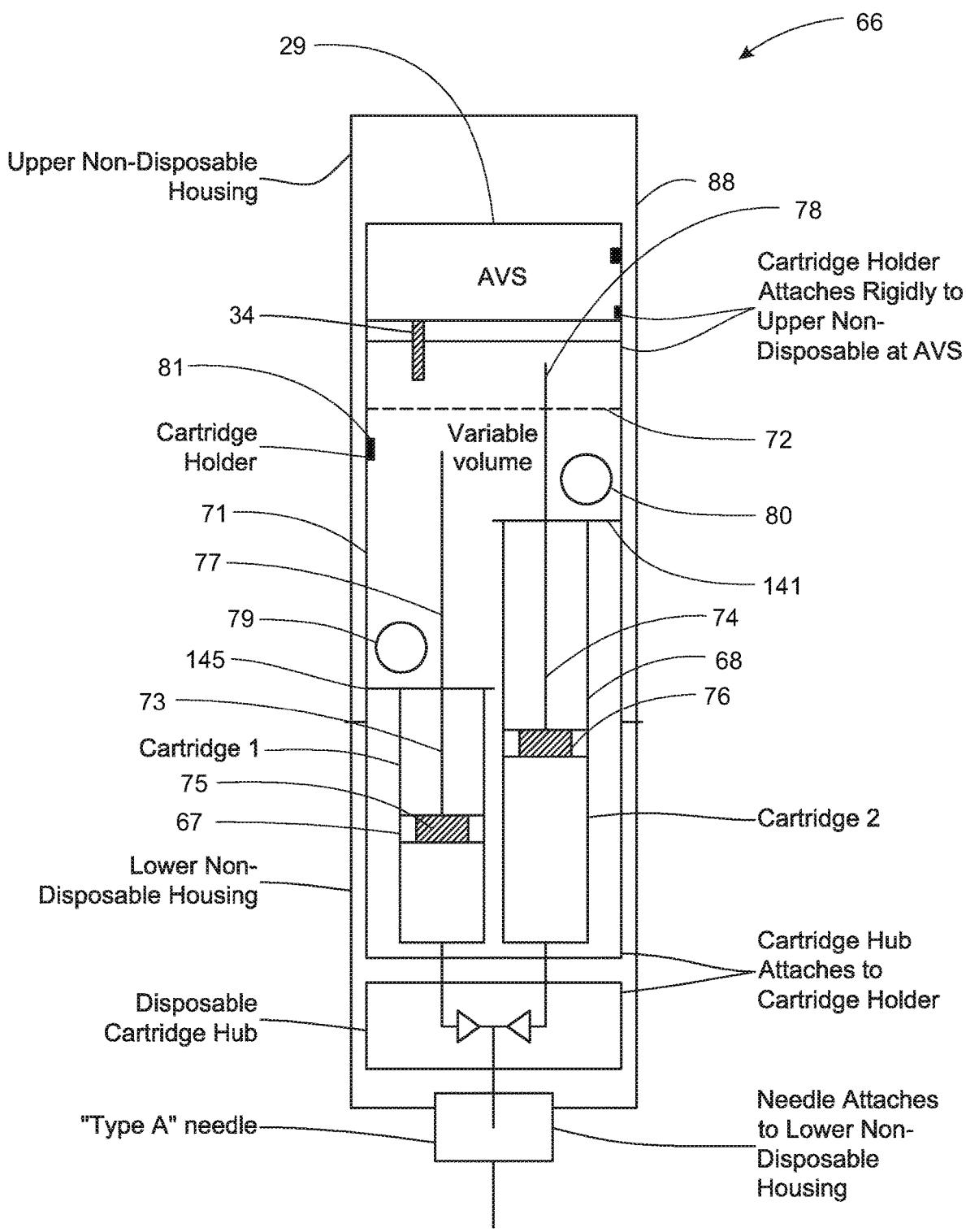
FIG. 5 shows an illustration of a syringe pump having two reservoirs disposed within an acoustic housing, and a reference-volume assembly coupled to the acoustic housing for acoustically estimating the amount of liquid discharged by the syringe pump in accordance with an embodiment of the present disclosure.

FIG. 5 shows an illustration of a syringe pump 66 having two reservoirs 67 and 68 disposed within an acoustic housing 71, and a reference-volume assembly 29 coupled to the acoustic housing 71 for acoustically estimating the amount of liquid discharged by the syringe pump 66 in accordance with an embodiment of the present disclosure. The syringe pump 66 may use acoustic volume sensing ("AVS") to estimate the volume of liquid within a reservoir 67, the volume of liquid within a reservoir 68, the volume of liquid discharged from the reservoir 67, and/or the volume of liquid discharged from the reservoir 68 using a speaker 36, a reference microphone 37, and a variable-volume microphone 81. The acoustic housing 71 may be attachable and/or disposable. For example, the acoustic housing 71 may snap fit into the housing 88. The housing 88 may be reusable and/or disposable. A manifold 61 and/or needle 109 may be attachable and/or disposable. A protection screen 72 prevents debris from entering into and/or affecting the acoustic port 39.

The syringe pump 66 includes reservoirs 67 and 68 disposed within the acoustic housing 71. The reservoir 67 has a piston 75 of a plunger 73 disposed therein. The reservoir 76 has a piston 76 of a plunger 74 disposed therein. The reservoir 67 has a stop 145 attached at an end thereof that prevents the piston 75 from moving out of the reservoir 67. Additionally, the reservoir 68 has a stop 146 attached at an end thereof that prevents the piston 76 from moving out of the reservoir 68.

The plunger 73 includes a shaft 77, and the plunger 74 includes a shaft 78 that are wholly disposed within the acoustic housing 71. Additionally, an actuator 79 is coupled to the shaft 77 to actuate the shaft 77, and another actuator 80 is coupled to the shaft 78 to actuate the shaft. Both of the actuators 79 and 80, and the two shafts 77 and 78 are disposed within the acoustic housing 71 in the embodiment shown in FIG. 5. Because the shafts 77 and 78, and the actuators 79 and 80 are disposed within the acoustic housing 71, movement of the shafts 77 and 78 and the actuators 79 and 80 (as liquid is discharged) does not affect the volume as sensed by the processor 21 of FIG. 2 (via the variable volume microphone 81 disposed within the acoustic housing 71); therefore, in the embodiment shown in the FIG. 5, the processor 21 of FIG. 2 does not have to compensate for varying volume caused by the movement of a shafts 77 and 78 and/or the actuators 79 and 80.

Figure 6:
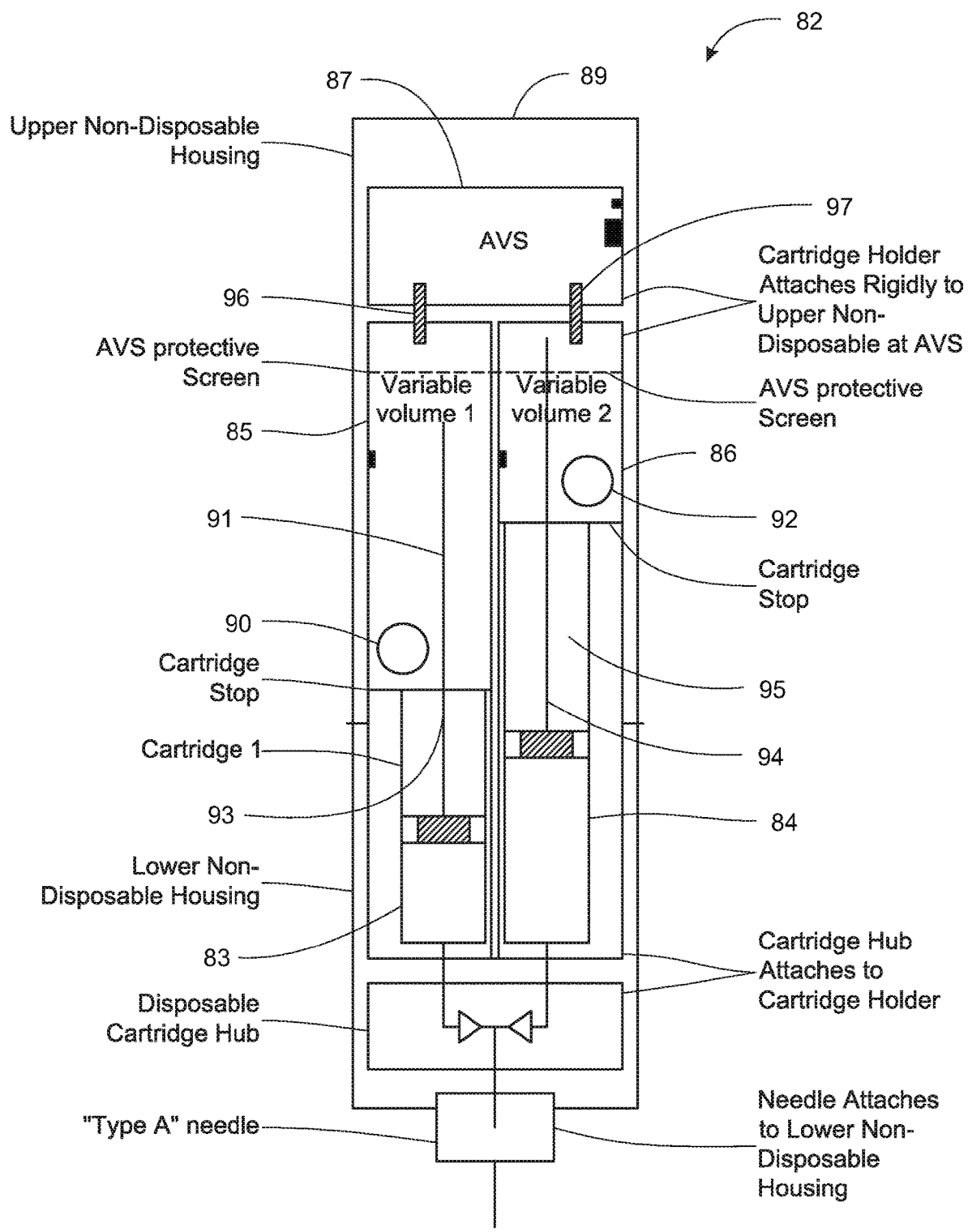
FIG. 6 shows an illustration of a syringe pump having two reservoirs each disposed within a respective acoustic housing, and a reference-volume assembly acoustically coupled to the acoustic housings for acoustically estimating the amount of liquid discharged by the syringe pump in accordance with an embodiment of the present disclosure.

FIG. 6 shows an illustration of a syringe pump 82 having two reservoirs 83 and 84 each disposed within a respective acoustic housing (85 and 86), and a reference-volume assembly 87 acoustically coupled to the acoustic housings 85 and 86 for acoustically estimating the amount of liquid discharged by the syringe pump 82 in accordance with an embodiment of the present disclosure. The syringe pump 82 may use acoustic volume sensing ("AVS") to estimate the volume of liquid within a reservoir 83, the volume of liquid within a reservoir 84, the volume of liquid discharged from the reservoir 83, and/or the volume of liquid discharged from the reservoir 84 using a speaker 36, a reference microphone 37, a variable-volume microphone 53, and a variable-volume microphone 54. The acoustic housings 85 and 86 may be removable, attachable, permanently fixed to the housing 89, and/or snap-fit into the housing 89. Additionally or alternatively, the reservoirs 83 and 84 may be removable, attachable, disposable, and/or may snap-fit into the housing 89. The manifold 61 and the needle 109 may be attachable and/or removable. The syringe pump includes 82 includes an actuator 90 coupled to a shaft 91 to actuate the shaft 91. The actuator 90 and the shaft 91 of the plunger 93 are disposed within the acoustic housing 85 thereby the processor 21 of FIG. 2 does not have to account for the movement of the shaft 91 and/or the actuator 90. The syringe pump includes 82 also includes an actuator 92 coupled to a shaft 94 to actuate the shaft 94. Likewise, the actuator 92 and the shaft 94 of the plunger 95 are disposed within the acoustic housing 86 thereby the processor 21 of FIG. 2 does not have to account for the movement of the shaft 94 and the actuator 92. The reference-volume assembly 87 is coupled to the acoustic housing 85 via an acoustic port 96 and to the acoustic housing 86 via another acoustic port 97

Figure 7:
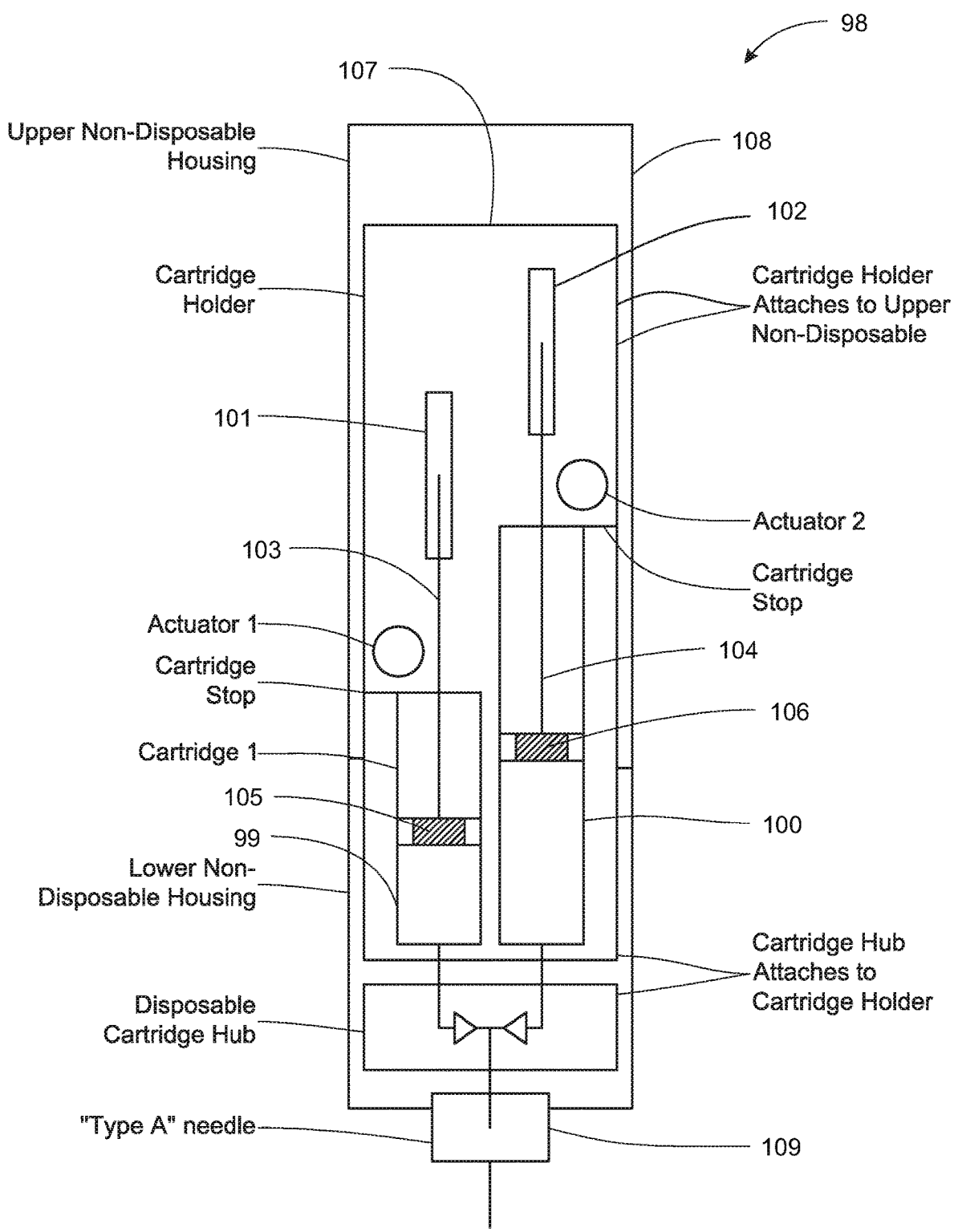
FIG. 7 shows an illustration of a syringe pump having two reservoirs and two capacitive sensors each coupled to a respective plunger of a respective reservoir for estimating the amount of liquid discharged by the syringe pump in accordance with an embodiment of the present disclosure.

FIG. 7 shows an illustration of a syringe pump 98 having two reservoirs 99 and 100 and two capacitive sensors 101 and 102 each coupled to a respective plunger 103 and 104 of a respective reservoir (99 and 199, respectively) for estimating the amount of liquid discharged by the syringe pump 98 in accordance with an embodiment of the present disclosure. The syringe pump 98 includes an actuator 90 coupled to the shaft of the plunger 103 to actuate the plunger 103. And, the syringe pump 98 also includes an actuator 92 coupled to the shaft of the plunger 104 to actuate the plunger 103.

The processor 21 of FIG. 2 may be coupled to the capacitive sensors 101 and 102 to determine the linear position of the plungers 103 and 104, and to estimate the volume that remains in the reservoirs 99 and 100. For example, the processor 21 may model the reservoir as a cylinder and may know how the feedback from the capacitors sensors 101 and 102 correspond to the position of the pistons 105 and 106 of the plungers 103 and 104, respectively. That is, the position of the pistons 105 and 106 may be used to estimate the volume of liquid in each of the reservoirs 99 and 100 by modeling the liquid side of the pistons 105 and 106 as cylinders.

The syringe pump 98 also includes a housing 107 that maybe be removable and/or disposable from the non-disposable housing 108. Additionally or alternatively, the syringe pump 98 also includes a manifold 153 that may be removable and/or disposable from the non-disposable housing 108. The syringe pump 98 may also optionally include a needle 109 that is coupled to the manifold 108. The needle 109 may be removable and/or disposable.

Figure 8:
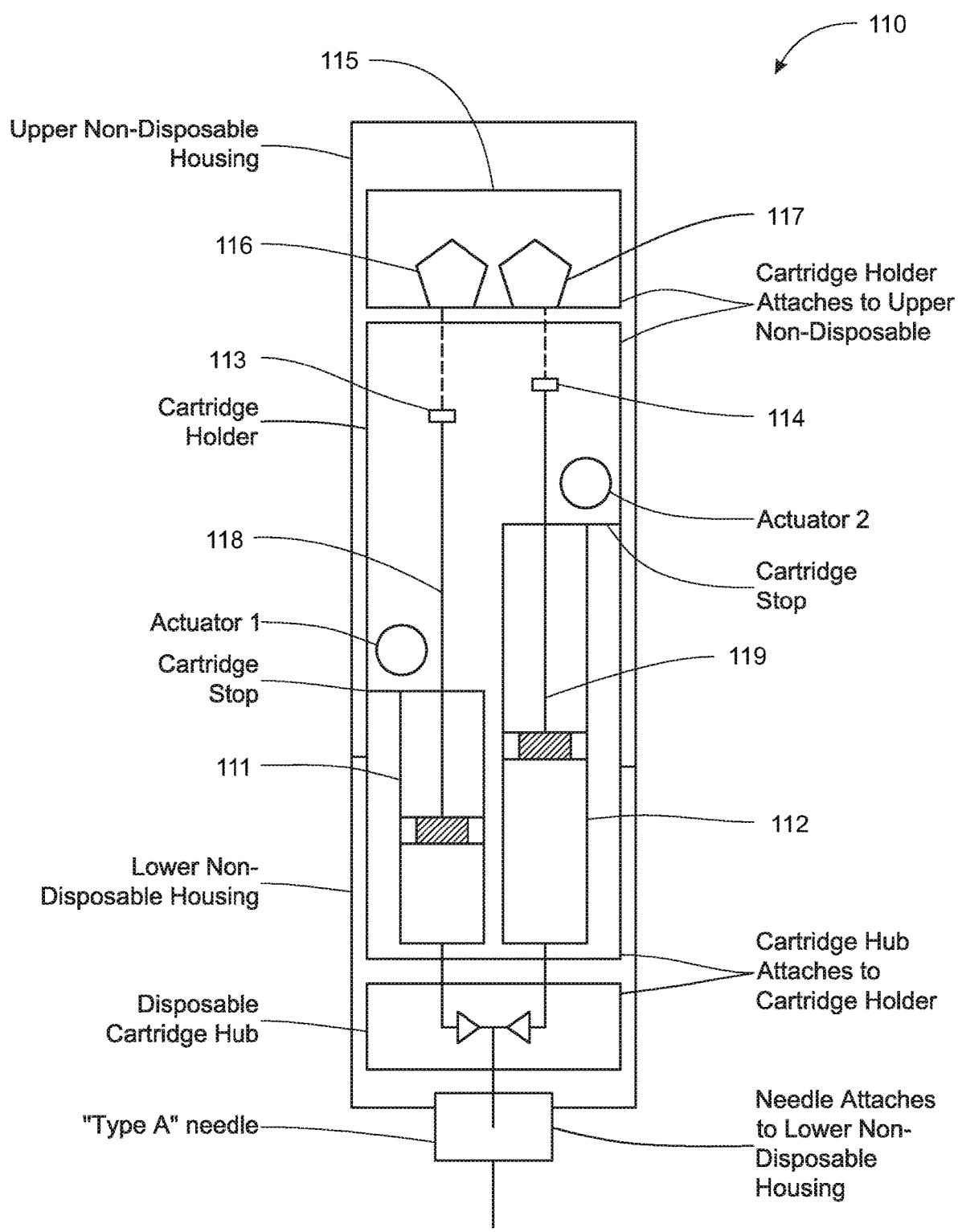
FIG. 8 shows an illustration of a syringe pump having two reservoirs and two reflective targets each coupled to a respective plunger of a respective reservoir for estimating the amount of liquid discharged by the syringe pump using an optical ranging assembly in accordance with an embodiment of the present disclosure.

FIG. 8 shows an illustration of a syringe pump 110 having two reservoirs 111 and 112 and two optical targets 113 and 114 each coupled to a respective plunger 118 or 119 of a respective reservoir (111 and 112, respectively) for estimating the amount of liquid discharged by the syringe pump 110 using an optical ranging assembly 115 in accordance with an embodiment of the present disclosure. The syringe pump 110 includes a housing 154 that may be attachable and/or removable (e.g., disposable) from an outer housing 155. Additionally or alternatively, the reservoirs 111 and 112 may be attachable and/or removable from the housing 154 (and may be disposable). The manifold 153 and/or the needle 109 may be attachable, removable, and/or disposable.

The syringe pump 110 includes an actuator 90 coupled to the shaft of the plunger 118 to actuate the plunger 118. And, the syringe pump 110 also includes an actuator 92 coupled to the shaft of the plunger 119 to actuate the plunger 119.

The processor 21 of FIG. 2 may estimate the amount of liquid in the reservoirs 111 and 112 similarly to the way as shown in the embodiment of FIG. 7. The optical ranging assembly includes two illuminators/sensors 116 and 117. The illuminator/sensor 116 shines a light on the optical target 113, which is reflected back to the illuminator/sensor 116. The optical ranging assembly 115 may use time of flight and/or intensity to estimate the position of the plunger 118. Likewise, the illuminator/sensor 117 shines a light on the optical target 114, which is reflected back to the illuminator/sensor 117. The optical ranging assembly 115 may use time of flight and/or intensity as received to estimate the position of the plunger 119.

The light from the illuminators/sensors 116 and 117 may be from an LED, laser, may be infrared, visible or invisible light, and may be modulated, e.g. to save power, etc.

Figure 9:
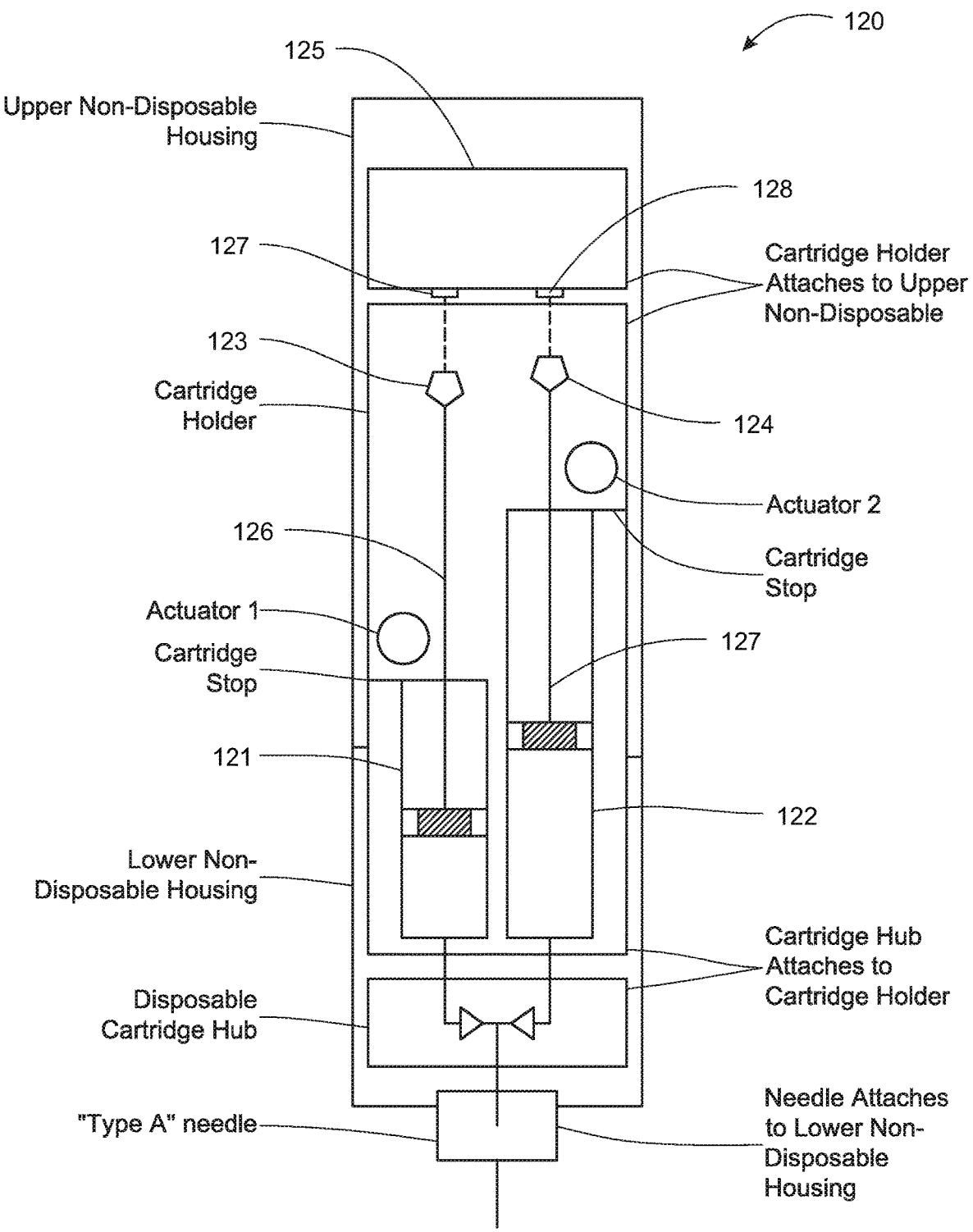
FIG. 9 shows an illustration of a syringe pump having two reservoirs and two light sources each coupled to a respective plunger of a respective reservoir for use with an optical ranging assembly for estimating the amount of liquid discharged by the syringe pump in accordance with an embodiment of the present disclosure.

FIG. 9 shows an illustration of a syringe pump 120 having two reservoirs 121 and 122 and two light sources 123 and 124 each coupled to a respective plunger 126 and 127 of a respective reservoir (121 and 122, respectively) for use with an optical ranging assembly 125 for estimating the amount of liquid discharged by the syringe pump in accordance with an embodiment of the present disclosure. The syringe pump 120 includes a housing 156 that may be attachable and/or removable (e.g., disposable) from an outer housing 157. Additionally or alternatively, the reservoirs 121 and 122 may be attachable and/or removable from the housing 156 (and may be disposable). The manifold 153 and/or the needle 109 may be attachable, removable, and/or disposable. The syringe pump 120 includes an actuator 90 coupled to the shaft of the plunger 126 to actuate the plunger 126. And, the syringe pump 120 also includes an actuator 92 coupled to the shaft of the plunger 127 to actuate the plunger 127.

The optical ranging assembly 126 includes sensors 128 and 160. The sensors 128 and 160 measure the intensity of the light sources 123 and 124 (e.g., LEDs) and correlates the measured intensity with a position of the plungers 126 and 127. The processor 21 may modulate the light sources 123 and 124 such that only one of the light sources 123 and 124 is active during a measurement of a respective sensors 128 and 160. In some embodiments, one of the light sources 123 and 124 may be active while both of the sensors 128 and 160 are used to estimate a position of a respective plunger (of plungers 126 and 127).

Figure 10:
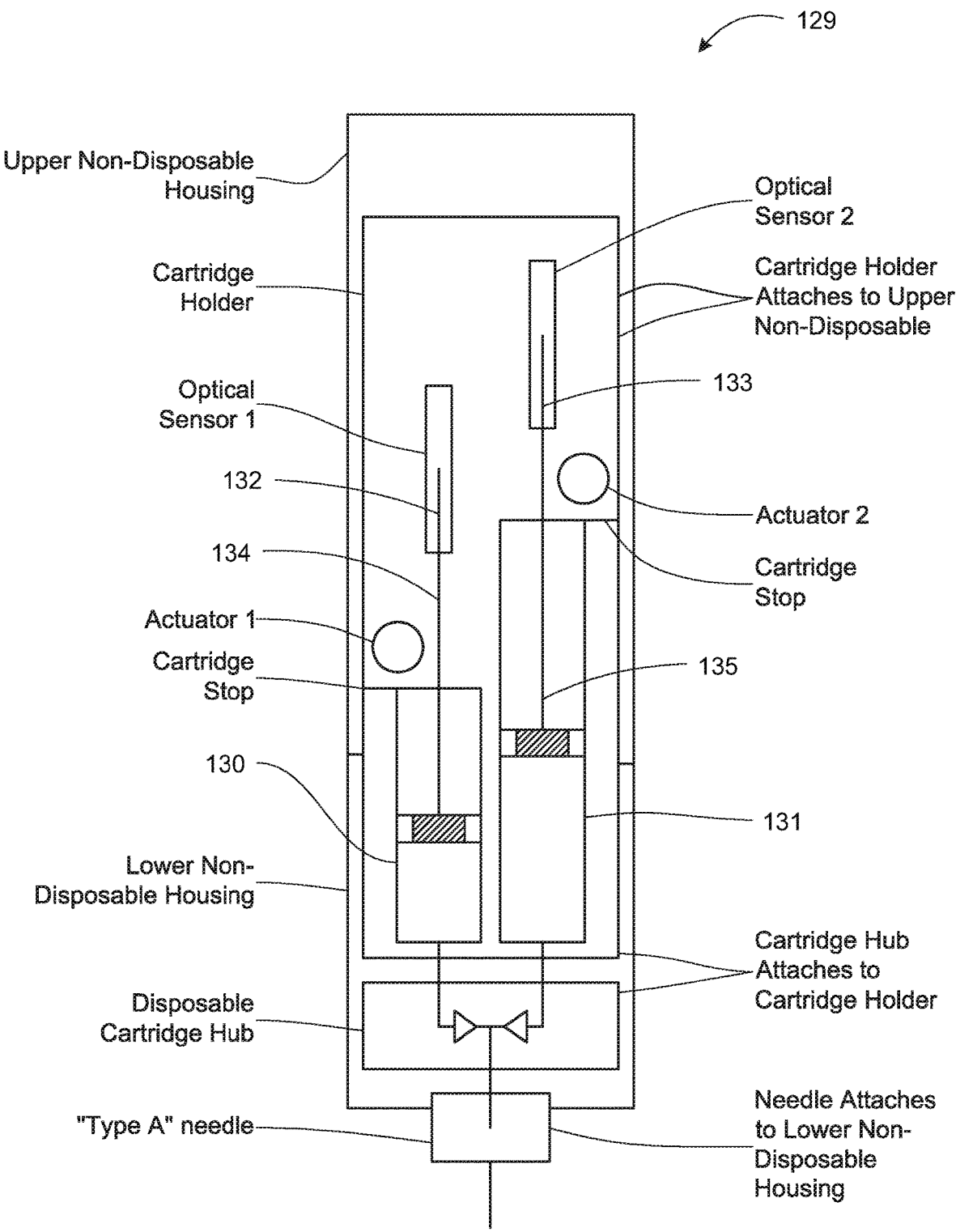
FIG. 10 shows an illustration of a syringe pump having two reservoirs and two linear optical position sensors each coupled to a respective plunger of a respective reservoir for estimating the amount of liquid discharged by the syringe pump in accordance with an embodiment of the present disclosure.

FIG. 10 shows an illustration of a syringe pump 129 having two reservoirs 130 and 131 and two linear optical position sensors 132 and 133 each coupled to a respective plunger (i.e., 134 and 135 respectively) of a respective reservoir (i.e., 130 and 131, respectively) for estimating the amount of liquid discharged by the syringe pump 129 in accordance with an embodiment of the present disclosure.

The syringe pump 129 includes a housing 158 that may be attachable and/or removable (e.g., disposable) from an outer housing 159. Additionally or alternatively, the reservoirs 130 and 131 may be attachable and/or removable from the housing 158 (and may be disposable). The manifold 153 and/or the needle 109 may be attachable, removable, and/or disposable.

The linear optical position sensors 132 and 133 may be a linear optical encoder. The processor 21 of FIG. 2 uses the feedback from the linear optical position sensors 132 and 133 to estimate the volume of liquid within the respective reservoirs 130 and 131, e.g., by cylinder volume approximation, or other geometry approximation.

Figure 11:
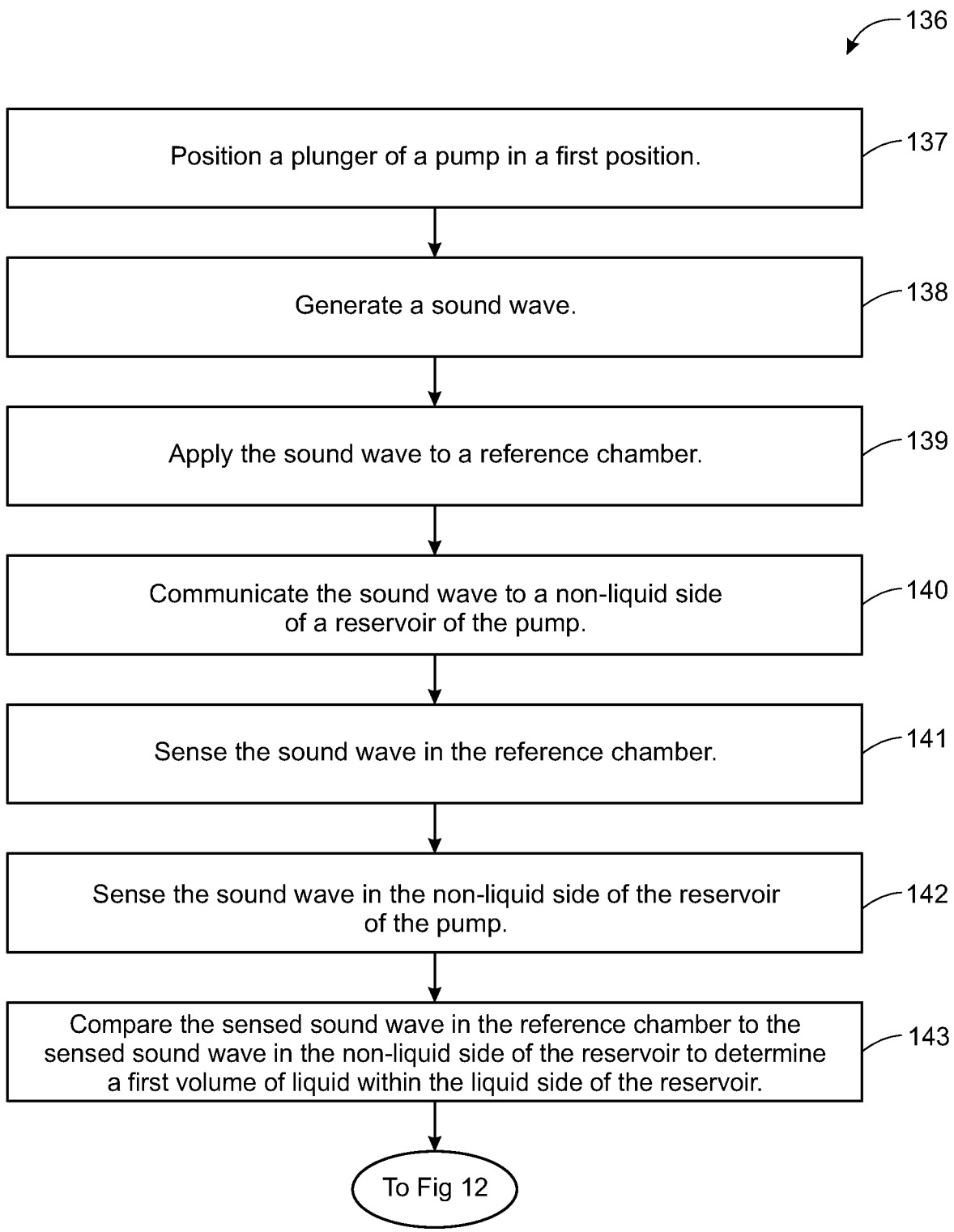
FIGS. 11-12 show a flow chart diagram of a method for estimating liquid delivery in accordance with an embodiment of the present disclosure.
Figure 12:
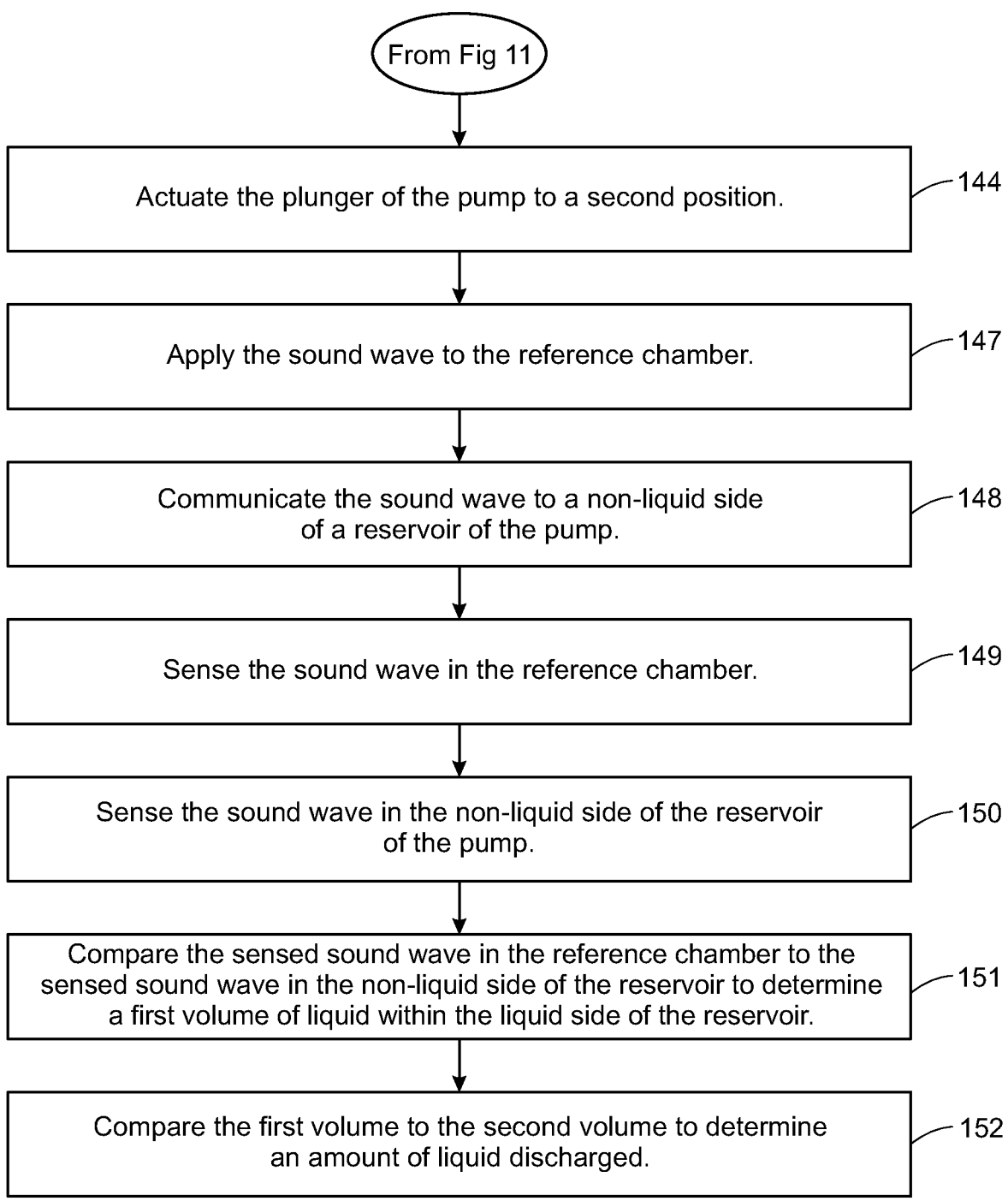

FIGS. 11-12 show a flow chart diagram of a method 136 for estimating liquid delivery in accordance with an embodiment of the present disclosure. The method 136 may be used with any pump disclosed herein, e.g., the syringe pump 10 of FIG. 1, the syringe pump 27 of FIG. 3, the syringe pump 42 of FIG. 4, the syringe pump 66 of FIG. 5, the syringe pump 82 of FIG. 6, the syringe pump 98 of FIG. 7, the syringe pump 110 of FIG. 8, the syringe pump 120 of FIG. 9, and/or the syringe pump 129 of FIG. 10.

Act 137 positions a plunger of a pump in a first position. Act 138 generates the sound wave. Act 139 applies the sound wave to a reference chamber. Act 140 communicates the sound wave to a non-liquid side of a reservoir of the pump. Act 141 senses the sound wave in the reference chamber. Act 142 senses the sound wave in the non-liquid side of the reservoir of the pump. Act 143 compares the sensed sound wave in the reference chamber to the sensed sound wave in the non-liquid side of the reservoir to determine a first volume of liquid within the liquid side of the reservoir. Act 144 actuates the plunger of the pump to a second position. Act 147 applies the sound wave to the reference chamber. Act 148 applies the sound wave to the non-liquid side of a reservoir of the pump. Act 149 senses the sound wave in the reference chamber. Act 150 senses the sound wave in the non-liquid side of the reservoir of the pump. Act 151 compares the sensed sound wave in the reference chamber to the sensed sound wave in the non-liquid side of the reservoir to determine a second volume of liquid within the liquid side of the reservoir. Act 152 compares the first volume to the second volume to determine an amount of liquid discharged.

Acoustic Volume Sensing

The follow discussion describes acoustic volume sensing that may be performed by the processor 21 of FIG. 2 with a speaker and two microphones (e.g., a reference microphone and a variable-volume microphone) of a syringe pump, e.g., syringe pump 27 of FIG. 3, syringe pump 42 of FIG. 3, syringe pump 66 of FIG. 5, and/or syringe pump 82 of FIG. 6; AVS may be used to estimate liquid within a reservoir disclosed herein, to estimate an amount of liquid discharged from a reservoir disclosed herein, and/or to estimate a liquid discharge rate of a reservoir disclosed herein. Table 1 shows the definition of various terms as follows:

TABLE 1

| Term | Definition |
| --- | --- |
| Symbols | |
| P | Pressure |
| p | Pressure Perturbation |
| V | Volume |
| v | Volume Perturbation |
| γ | Specific Heat Ratio |
| R | Specific Gas Constant |
| ρ | Density |
| Z | Impedance |
| f | Flow friction |
| A | Cross sectional Area |
| L | Length |

TABLE 1-continued

| Term | Definition |
| --- | --- |
| ω | Frequency |
| ζ | Damping ratio |
| α | Volume Ratio |
| Subscripts | |
| 0 | Speaker Volume |
| 1 | Reference Volume |
| 2 | Variable Volume |
| k | Speaker |
| r | Resonant Port |
| z | Zero |
| p | Pole |

The acoustic volume sensor ("AVS") measures the fluid volume displaced by the non-liquid side of a reservoir in the AVS chamber, e.g., an acoustic housing or within a reservoir, etc. The sensor does not directly measure the fluid volume, but instead measures the variable volume of air, V2, within the AVS chamber; if the total volume of AVS chamber remains constant, the change in the V2 will be the direct opposite of the change in the fluid volume. The AVS chamber is the volume of air in fluid communication with a variable-volume microphone beyond the acoustic port. For example, in FIG. 3, the non-liquid side 32 of the reservoir 29 is the variable volume and the reference volume 35 is V1.

The volume of air, V2, is measured using an acoustic resonance. A time-varying pressure is established in the fixed volume of the reference chamber, V1, using a speaker. This pressure perturbation causes cyclic airflow in the acoustic port connecting the two volumes, which in turn causes a pressure perturbation in the variable volume. The system dynamics are similar to those of a Helmholtz oscillator; the two volumes act together as a "spring" and the air in the port connecting the volumes as a resonant mass. The natural frequency of this resonance is a function of the port geometry, the speed of sound, and the variable volume. The port geometry is fixed and the speed of sound can be found by measuring the temperature; therefore, given these two parameters, the variable volume can be found from the natural frequency. In some embodiments of the present disclosure, a temperature sensor is used within the acoustic housing and/or within the non-liquid side of a reservoir. In some embodiments, the temperature is considered to be a predetermined fixed value, e.g., is assumed to be room temperature, etc.

The natural frequency of the system is estimated by measuring the relative response of the pressures in the two volumes to different frequency perturbations created by the speaker. A typical AVS measurement will consist of taking an initial measurement. The liquid is then released from the liquid side of one or more reservoirs and delivered to the patient (after which a second volume measurement is taken). The difference between these measurements will be the volume of liquid delivered to the patient. In some embodiments a measurement will be taken before filling the liquid side of the one or more reservoirs and/or prior to discharging the liquid, e.g., when the syringe pump is preloaded, to detect any failures of the fluidic system.

An AVS measurement may occur in accordance with the following acts: (1) the processor 21 will turn on power to the AVS electronics, enable the ADC of the processor 21 of FIG. 2, and initialize an AVS algorithm; (2) an AVS measurement consists of collecting data at a number of different frequencies; (3) optionally measuring the temperature; and (4) then running an estimation routine based on the collected data to estimate the volume of liquid in the liquid side of a reservoir.

To collect data at each frequency, the speaker is driven sinusoidally at the target frequency and measurements are taken from the two microphones over an integer number of wavelengths, e.g., the reference microphone and the variable volume microphone (as described above). Once the data has been collected, the processor 21 of FIG. 1 performs a discrete Fourier transform algorithm on the data to turn the time-series data from the microphones into a single complex amplitude. Integrity checks are run on the data from the microphones to determine if the data is valid, e.g., the response is within a predetermined phase and/or amplitude range of the acoustic frequency.

The frequency measurements are taken at a number of different frequencies. This sine-sweep is then used by the estimation routine to estimate the variable volume. After the estimation is complete, other integrity checks is may be performed on the whole sine sweep, including a secondary check by the processor 21 of FIG. 2.

In some embodiments, after the processor 21 of FIG. 2 verifies the measurement integrity, the volume estimates are finalized and the sensor is powered off.

AVS Resonance Model

The governing equations for the AVS system can be found from first-principles given a few simplifying assumptions. The system is modeled as two linearized acoustic volumes connected by an idealized acoustic port.

Modeling the Acoustic Volumes

The pressure and volume of an ideal adiabatic gas can be related by Equation 1 as follows:

$$PV^\gamma = K \quad (1)$$

where K is a constant defined by the initial conditions of the system. Equation 1 can be written in terms of a mean pressure, P, and volume, V, and a small time-dependent perturbation on top of those pressures, p(t), v(t) as illustrated in Equation 2 as follows:

$$(P+p(t))(V+v(t))^\gamma = K \quad (2)$$

Differentiating Equation 2 results in Equation 3 as follows:

$$\dot{p}(t)(V+v(t))^\gamma + \gamma(V+v(t))^{\gamma-1}(P+p(t))\dot{v}(t) = 0 \quad (3)$$

Equation 3 simplifies to Equation 4 as follows:

$$\dot{p}(t) + \gamma \frac{P + p(t)}{V + v(t)} \dot{v}(t) = 0. \quad (4)$$

If the acoustic pressure levels are much less than the ambient pressure the Equation 4 can be further simplified to Equation 5 as follows:

$$\dot{p}(t) + \frac{\gamma P}{V} \dot{v}(t) = 0. \quad (5)$$

Using the adiabatic relation, Equation 6 can be shown as follows:

$$\frac{P}{V} = \left(\frac{P + p(t)}{V + v(t)}\right)\left(\frac{P + p(t)}{P}\right)^{\frac{\gamma+1}{\gamma}}. \quad (6)$$

Thus, the error assumption is shown in Equation 7 as follows:

$$\text{error} = 1 - \left(\frac{P + p(t)}{P}\right)^{\frac{\gamma+1}{\gamma}}. \quad (7)$$

A very loud acoustic signal (e.g., 120 dB) would correspond to pressure sine wave with amplitude of roughly 20 Pascal. Assuming air at atmospheric conditions has the parameters of $\gamma=1.4$ and $P=101325$ Pa, the resulting error is 0.03%. The conversion from dB to Pa is shown in Equation 8 as follows:

$$\gamma = 20\log_{10}\left(\frac{p_{rms}}{p_{ref}}\right) \quad (8)$$

or $$p_{rms} = p_{ref} 10^{\frac{\lambda}{20}},$$

where $$p_{ref} = 20 \cdot \mu\text{Pa}.$$

Applying the ideal gas law, $P=\rho RT$, and substituting in for pressure gives the result as shown in Equation 9 as follows:

$$\dot{p}(t) + \frac{\gamma RT \rho}{V} \dot{v}(t) = 0. \quad (9)$$

This can be written in terms of the speed of sound in Equation 10 as follows:

$$a = \sqrt{\gamma RT} \quad (10).$$

And, substituting in Equation 10 in Equation 9 results in Equation 11 as follows:

$$\dot{p}(t) + \frac{\rho a^2}{V} \dot{v}(t) = 0. \quad (11)$$

Acoustic impedance for a volume is defined in Equation 12 as follows:

$$Z_v = \frac{p(t)}{\dot{v}(t)} = -\frac{1}{\left(\frac{V}{\rho a^2}\right)s}. \quad (12)$$

Modeling the Acoustic Port

The acoustic port is modeled assuming that all of the fluid in the port essentially moves as a rigid cylinder reciprocating in the axial direction. All of the fluid in the channel is assumed to travel at the same velocity, the channel is assumed to be of constant cross section, and the end effects resulting from the fluid entering and leaving the channel are neglected.

If we assume laminar flow friction of the form $\Delta P = f \rho \dot{v}$, the friction force acting on the mass of fluid in the channel can be written: $F = f \rho A^2 \dot{x}$.

A second order differential equation can then be written for the dynamics of the fluid in the channel as shown in Equation 13 as follows:

$$\rho L A \ddot{x} = \Delta p A - f \rho A^2 \dot{x} \quad (13),$$

or, in terms of volume flow rate as shown in Equation 14 as follows:

$$\ddot{v} = -\frac{fA}{L}\dot{v} + \Delta p \frac{A}{\rho L}. \quad (14)$$

The acoustic impedance of the channel can then be written as shown in Equation 15:

$$Z_p = \frac{\Delta p}{\dot{v}} = \frac{\rho L}{A}\left(s + \frac{fA}{L}\right). \quad (15)$$

System Transfer Functions

Using the volume and port dynamics define above, the AVS system can be described by the following system of Equations 16-19:

$$\dot{p}_0 - \frac{\rho a^2}{V_0} \dot{v}_k = 0, \quad (16)$$

$$\dot{p}_1 + \frac{\rho a^2}{V_1} (\dot{v}_k - \dot{v}_r) = 0, \quad (17)$$

$$\dot{p}_2 + \frac{\rho a^2}{V_2} \dot{v}_r = 0, \quad (18)$$

and $$\ddot{v}_r = -\frac{fA}{L}\dot{v}_r + \frac{A}{\rho L}(p_2 - p_1). \quad (19)$$

One equation can be eliminated if $p_0$ is treated as the input substituting in $$\dot{v}_k = \frac{V_0}{\rho a^2} \dot{p}_0$$

as shown in Equations 20-22:

$$\dot{p}_1 + \frac{V_0}{V_1} \dot{p}_0 - \frac{\rho a^2}{V_1} \dot{v}_r = 0, \quad (20)$$

$$\dot{p}_2 + \frac{\rho a^2}{V_2} \dot{v}_r = 0, \text{ and} \quad (21)$$

$$\ddot{v}_r = -\frac{fA}{L}\dot{v}_r + \frac{A}{\rho L} p_2 - \frac{A}{\rho L} p_1. \quad (22)$$

The relationship between the two volumes on each side of the acoustic port is referred to as the Cross Port transfer function. This relationship is illustrated in Equation 23 as follows:

$$\frac{p_2}{p_1} = \frac{\omega_n^2}{s^2 + 2\zeta\omega_n s + \omega_n^2}, \text{ where} \quad (23)$$

$$\omega_n^2 = \frac{a^2 A}{L} \frac{1}{V_2} \text{ and } \zeta = \frac{fA}{2L\omega_n}.$$

This relationship has the advantage that the poles are only dependent on the variable volume and not on the reference volume. Note that the resonant peak is actually due to the inversion of the zero in the response of the reference volume pressure. This means that that pressure measurement in the reference chamber will have a low amplitude in the vicinity of the resonance which may influence the noise in the measurement.

Resonance Q Factor and Peak Response

The quality of the resonance is the ratio of the energy stored to the power loss multiplied by the resonant frequency. For a pure second-order system the quality factor can be expressed as a function of the damping ratio illustrated in Equation 24:

$$Q = \frac{1}{2\zeta}. \tag{24}$$

The ratio of the peak response to the low-frequency response can also be written as a function of the damping ratio shown in Equation 25:

$$|G|_{\omega_d} = \frac{1}{\zeta\sqrt{5-4\zeta}}. \tag{25}$$

This will occur at the damped natural frequency $\omega_d = \omega_n \sqrt{1-\zeta}$.

Electrical and Mechanical Analogies

The acoustic resonator is analogous to either a spring-mass-damper system or a LRC circuit, e.g., a resistor, inductor and capacitor coupled together in series, for example.

Computing the Complex Response

To implement AVS, the system must get the relative response of the two microphones to the acoustic wave set up by the speaker. This is accomplished by driving the speaker with a sinusoidal output at a known frequency; the complex response of each microphone is then found at that driving frequency. Finally, the relative responses of the two microphones are found and corrected for alternating sampling of the analog-to-digital converter coupled to the processor 21 of FIG. 2.

In addition, the total signal variance is computed and compared to the variance of pure tone extracted using the discrete Fourier transform ("DFT"). This gives a measure of how much of the signal power comes from noise sources or distortion. In some embodiments of the present disclosure, this value can be used to reject and repeat bad measurements.

Computing the Discrete Fourier Transform

The signal from each microphone is sampled synchronously with the output to the speaker such that a fixed number of points, N, are taken per wavelength. The measured signal at each point in the wavelength is summed over an integer number of wavelengths, M, and stored in an array x by an interrupt service routine ("ISR") in the processor 21 of FIG. 2 after all the data for that frequency has been collected.

A discrete Fourier transform is done on the data at the integer value corresponding to the driven frequency of the speaker. The general expression for the first harmonic of a DFT is as follows in Equation 26:

$$x_k = \frac{2}{MN}\sum_{n=0}^{N-1} x_n e^{-\frac{2\pi i}{N}kn}. \tag{26}$$

The product MN is the total number of points and the factor of 2 is added such that the resulting real and imaginary portions of the answer match the amplitude of the sine wave illustrated in Equation 27:

$$x_n = \text{re}(x_k)\cos\left(\frac{2\pi}{N}kn\right) + \text{im}(x_k)\sin\left(\frac{2\pi}{N}kn\right). \tag{27}$$

This real part of this expression is illustrated in Equation 28:

$$\text{re}(x) = \frac{2}{MN}\sum_{n=0}^{N-1} x_n \cos\left(\frac{2\pi}{N}n\right). \tag{28}$$

We can take advantage of the symmetry of the cosine function to reduce the number of computations needed to compute the DFT. The expression above is equivalent to Equation 29 as follows:

$$\text{re}(x) = \frac{2}{MN}\left[\left(x_0 - x_{\frac{1}{2}N}\right) + \sum_{n=1}^{\frac{1}{4}N-1}\sin\left(\frac{\pi}{2} - \frac{2\pi}{N}n\right)\left[\left(x_n - x_{\frac{1}{2}N+n}\right) - \left(x_{\frac{1}{2}N-n} - x_{N-n}\right)\right]\right]. \tag{29}$$

Similarly, the imaginary portion of the equation is illustrated in Equation 30 as follows:

$$\text{im}(x) = -\frac{2}{MN}\sum_{n=0}^{N-1} x_n \sin\left(\frac{2\pi}{N}n\right), \tag{30}$$

which may be expressed as Equation 31:

$$\text{im}(x) = \frac{2}{MN}\left[\left(x_{\frac{1}{4}N} - x_{\frac{3}{4}N}\right) + \sum_{n=1}^{\frac{1}{4}N-1}\sin\left(\frac{2\pi}{N}n\right)\left[\left(x_n - x_{\frac{1}{2}N+n}\right) + \left(x_{\frac{1}{2}N-n} - x_{N-n}\right)\right]\right]. \tag{31}$$

The variance of the signal at that driven frequency is illustrated in Equation 32 as follows:

$$\sigma_{tone}^2 = \tfrac{1}{2}(\text{re}(x)^2 + \text{im}(x)^2) \tag{32}.$$

The tone variance is proportional to the acoustic power at the driven frequency. The maximum possible value of the real and imaginary portions of x is $2^{11}$; this corresponds to half the A/D range. The maximum value of the tone variance is $2^{21}$; half the square of the AD range.

Computing the Total Signal Variance

A good measure of the integrity of a measurement is the ratio of the acoustic power at the driven frequency relative to the total acoustic power at all frequencies. The total signal variance is given by the expression in Equation 33:

$$\sigma_{total}^2 = \frac{1}{NM}\sum_{n=0}^{MN-1} p_n^2 - \overline{p}^2 = \frac{1}{NM}\sum_{n=0}^{MN-1} p_n^2 - \left(\frac{1}{NM}\sum_{n=0}^{MN-1} p_n\right)^2. \quad (33)$$

However, in some specific embodiments, the summations are performed in the A/D interrupt service routine (ISR) where there are time constraints and/or all of the microphone data must be stored for post-processing. In some embodiments, to increase efficiency, a pseudo-variance is calculated based on a single averaged wavelength. The pseudo-variance of the signal is calculated using the following relation illustrated in Equation 34 as follows:

$$\sigma_{total}^2 = \frac{1}{NM^2}\sum_{n=0}^{N-1} x_n^2 - \frac{1}{N^2M^2}\left(\sum_{n=0}^{N-1} x_n\right)^2. \quad (34)$$

The result is in the units of AD counts squared. The summation will be on the order of $$\sum_{n=0}^{N-1} x_n^2 = O(NM^2 2^{24})$$

for a 12-bit ADC. If $N<2^7=128$ and $M<2^6=64$ then the summation will be less than $2^{43}$ and can be stored in a 64-bit integer. The maximum possible value of the variance would result if the ADC oscillated between a value of 0 and $2^{12}$ on each consecutive sample. This would result in a peak variance of $\frac{1}{4}(2^{12})^2=2^{22}$ so the result can be stored at a maximum of a Q9 resolution in a signed 32-bit integer.

Computing the Relative Microphone Response

The relative response of the two microphones, G, is then computed from the complex response of the individual microphones illustrated in Equations 35-37:

$$G = \frac{x_{var}}{X_{ref}} = \frac{x_{var}}{x_{ref}}\frac{x_{ref}^*}{x_{ref}^*}. \quad (35)$$

$$\text{Re}(G) = \frac{\text{Re}(x_{var})\text{Re}(x_{ref}) + \text{Im}(x_{var})\text{Im}(x_{ref})}{\text{Re}(x_{ref})^2 + \text{Im}(x_{ref})^2}. \quad (36)$$

$$\text{Im}(G) = \frac{\text{Re}(x_{ref})\text{Im}(x_{var}) - \text{Re}(x_{var})\text{Im}(x_{ref})}{\text{Re}(x_{ref})^2 + \text{Im}(x_{ref})^2}. \quad (37)$$

The denominator of either expression can be expressed in terms of the reference tone variance computed in the previous section, illustrated as follows in Equation 38:

$$\text{Re}(x_{ref})^2 + \text{Im}(x_{ref})^2 = 2\sigma_{ref}^2 \quad (38).$$

Correcting for A/D Skew

The speaker output may be updated at a fixed 32 times per sample. For example, as the driving frequency is changed, the speaker output frequency is also updated to maintain the fixed 32 cycles. The two microphones are sampled synchronous with the speaker output so the sampling frequency remains at a fixed interval of the driving frequency. The microphone A/D measurements, however, are not sampled simultaneously; the A/D ISR alternates between the two microphones, taking a total of N samples per wavelength for each microphone. The result will be a phase offset between the two microphones of $$\frac{\pi}{N}.$$

To correct for this phase offset, a complex rotation is applied to the relative frequency response computed in the previous section.

To rotate a complex number an angle $$\frac{\pi}{N}$$

it is multiplied by $$e^{i\frac{\pi}{N}} = \cos\left(\frac{\pi}{N}\right) + i\sin\left(\frac{\pi}{N}\right).$$

The result is illustrated in Equation 39 as follows:

$$G_{rotated} = \left(\text{Re}(G)\cos\left(\frac{\pi}{N}\right) - \text{Im}(G)\sin\left(\frac{\pi}{N}\right)\right) + \left(\text{Im}(G)\cos\left(\frac{\pi}{N}\right) + \text{Re}(G)\sin\left(\frac{\pi}{N}\right)\right)i. \quad (39)$$

Time Delays

In some embodiments, one of the assumptions when deriving the AVS equations is that the pressure is uniform in the acoustic volumes. This assumption is true if the acoustic wavelength is large compared to the dimensions of the AVS chamber. The wavelength of a sound wave at a given frequency can be computed with the following Equation 40:

$$\lambda = \frac{a}{f}. \quad (40)$$

For example, the wavelength at 1 kHz is roughly 246 mm and at 5 kHz is roughly 49.2 mm. The AVS chamber may have a diameter such that the time delay associated with acoustic waves traveling through the volumes has a small but measurable effect. The effect can be modeled as a time delay (or time advance, depending on microphone orientation). The Laplace transform of a pure time delay, d, is illustrated in Equation 41 as follows:

$$G = e^{ds} \quad (41).$$

The phase is influenced by the time delay, but not the magnitude of system response. To correct for the time delays, the frequency response data may be corrected in advance by applying a model fit algorithm. The complex amplitude may be rotated as a function of frequency according the time delay equation above. The time delay may be assumed to be fixed, so the rotation is only a function of frequency.

The time delay may be determined by running an optimization routine to find the time delay to minimize the model fit error. Additionally or alternatively, there may be an apparent "time advance" in the data. For example, the reference microphone may experience a pressure perturbation slightly in advance of the acoustic port and the variable microphone may experience a pressure perturbation slightly behind the acoustic port. These "advances" and "delays" may be the effects of the propagation of the pressure waves and are in addition to "resonant" dynamics of the system, e.g., these effects may be accounted for.

Amplitude Leveling

The amplitude of the pressure measurements for a given speaker drive signal may vary from device-to-device and also as a function of the driven frequency. The device-to-device variations result from part-to-part differences in microphone and speaker sensitivities (e.g., roughly on the order of +/−3 dB). The frequency-based dependencies result from variations in speaker sensitivity over frequency as well as from the expected dynamics of the acoustic resonance.

To compensate, in some embodiments, the speaker gain is automatically tuned during the AVS measurement. The speaker gains are stored in an array with one entry for each of the sine-sweep frequencies, e.g., within the memory 22 of FIG. 2. The amplitude of the microphone signal (from either the variable or reference microphone) may be checked against the target amplitude. If it is either too large or too small a binary search routine may be employed to update the speaker gain at that frequency.

Checking Individual Measurement Integrity

It is possible for component errors, failures, or external disturbances to result in an erroneous measurement. Component failures might include a distorted speaker output or failed microphone. External disturbances might include mechanical shock to the pump housing or an extremely loud external noise. These types of failures can be detected using two different integrity checks: microphone saturation and out-of-band variance.

The microphone saturation check looks at the maximum and minimum values of the wavelength averaged signal for each microphone. If these values are close to the limits of the A/D then a flag within the processor 21 of FIG. 2 is set indicating that the measurement amplitude was out of range.

The out-of-band variance check compares the tone variance to the total signal variance for each microphone. In the ideal case the ratio of these signals will be 1—all of the acoustic power will be at the driven frequency. In the event of shock or an extremely loud external acoustic noise, more power will be present at other frequencies and this value will be lower than unity. In some embodiments, normal operation may be considered to have a ratio greater than 0.99.

In some embodiments, if an individual data point fails either of these integrity checks, it may be repeated or excluded without having to repeat the entire sine-sweep to help facilitate AVS robustness. Other integrity checks may be done based on the complete sine-sweep and are described later.

Volume Estimation Using Swept Sine-Generalized Solution

The resonant frequency of the system may be estimated using swept-sine system identification. In this method the response of the system to a sinusoidal pressure variation may be found at a number of different frequencies. This frequency response data may be then used to estimate the system transfer function using linear regression.

The transfer function for the system can be expressed as a rational function of s. The general case is expressed below for a transfer function with an $n^{th}$ order numerator and an $m^{th}$ order denominator. N and D are the coefficients for the numerator and denominator respectively. The equation has been normalized such that the leading coefficient in the denominator is 1, as illustrated in Equations 42 and 43:

$$G(s) = \frac{N_n s^n + N_{n-1} s^{n-1} + \ldots + N_0}{s^m + D_{m-1} s^{m-1} + D_{m-2} s^{m-2} + \ldots + D_0} \quad (42)$$

or $$G(s) = \frac{\sum_{k=0}^{n} N_k s^k}{s^m + \sum_{k=0}^{m-1} D_k s^k}. \quad (43)$$

This equation can be re-written in the form of Equation 44 as follows:

$$Gs^m = \sum_{k=0}^{n} N_k s^k - G \sum_{k=0}^{m-1} D_k s^k. \quad (44)$$

Equation 45 shows this summation in matrix notation:

$$\begin{bmatrix} G_1 s_1^m \\ \vdots \\ G_k s_k^m \end{bmatrix} = \begin{bmatrix} s_1^n & \ldots & s_1^0 & -G_1 s_1^{m-1} & \ldots & -G_1 s_1^0 \\ \vdots & & \vdots & \vdots & & \vdots \\ s_k^n & \ldots & s_k^0 & -G_k s_k^{m-1} & \ldots & -G_k s_k^0 \end{bmatrix} \begin{bmatrix} N_n \\ \vdots \\ N_0 \\ D_{m-1} \\ \vdots \\ D_0 \end{bmatrix}. \quad (45)$$

Where k is the number of data points collected in the swept sine. To simplify the notation this equation can be summarized using the vectors y illustrated in Equation 46.

$$y = Xc \quad (46).$$

Where y is k by 1, x is k by (m+n−1) and c is (m+n−1) by 1. The coefficients can then be found using a least square approach. The error function can be written as shown in Equation 47:

$$e = y - Xc \quad (47).$$

The function to be minimized is the weighted square of the error function; W is a k×k diagonal matrix, as illustrated in Equations 48-49.

$$e^T We = (y - Xc)^T W(y - Xc) \quad (48).$$

$$e^T We = y^T Wy - (y^T WXc)^T - y^T WXc + c^T x^T WXc \quad (49).$$

The center two terms are scalars so the transpose can be neglected, as illustrated in Equations 50-52:

$$e^T We = y^T Wy - 2y^T WXc + c^T x^T WXc, \quad (50)$$

$$\frac{\partial e^T We}{\partial c} = -2X^T Wy + 2X^T WXc = 0, \text{ and} \quad (51)$$

$$c = (X^T WX)^{-1} X^T Wy. \quad (52)$$

In some embodiments, the complex transpose in all of these cases is utilized. This approach can result in complex coefficients, but the process can be modified to ensure that all the coefficients are real. The least-square minimization can be modified to give only real coefficients if the error function is changed to Equation 53.

$$e^T W e = \text{Re}(y-Xc)^T W \, \text{Re}(y-Xc) + \text{Im}(y-Xc)^T W \, \text{Im}(y-Xc) \quad (53).$$

Then the coefficients can be found with the Equation 54:

$$c = (\text{Re}(X)^T W \, \text{Re}(X) + \text{Im}(X)^T W \, \text{Im}(X))^{-1}(\text{Re}(X)^T W \, \text{Re}(y) + \text{Im}(X)^T W \, \text{Im}(y)) \quad (54).$$

Volume Estimation Using Swept Sine-Solution for a $2^{nd}$ Order System

For a system with a $0^{th}$ order numerator and a second order denominator as shown in the transfer function illustrated in Equation 55.

$$G(s) = \frac{N_0}{s^2 + D_1 s + D_0}. \quad (55)$$

The coefficients in this transfer function can be found based on the expression found in the previous section as follows (Equation 56):

$$c = (\text{Re}(X)^T W \, \text{Re}(X) + \text{Im}(X)^T W \, \text{Im}(X))^{-1}(\text{Re}(X)^T W \, \text{Re}(y) + \text{Im}(X)^T W \, \text{Im}(y)) \quad (56).$$

Where Equation 57 is as follows:

$$y = \begin{bmatrix} G_1 s_1^2 \\ \vdots \\ G_k s_k^2 \end{bmatrix}, X = \begin{bmatrix} 1 & -G_1 s_1 & -G_1 \\ \vdots & \vdots & \vdots \\ 1 & -G_k s_k & -G_k \end{bmatrix}, \text{ and } c = \begin{bmatrix} N_0 \\ D_1 \\ D_0 \end{bmatrix}. \quad (57)$$

To simplify the algorithm we can combine some of terms as illustrated in Equations 58-60:

$$c = D^{-1} b \quad (58),$$

where $$D = \text{Re}(X)^T W \, \text{Re}(X) + \text{Im}(X)^T W \, \text{Im}(X) \quad (59), \text{ and}$$

$$b = \text{Re}(X)^T W \, \text{Re}(y) + \text{Im}(X)^T W \, \text{Im}(y) \quad (60).$$

To find an expression for D in terms of the complex response vector G and the natural frequency $s=j\omega$ we first split X into its real and imaginary parts as illustrated in Equations 61 and 62, respectively, as follows:

$$\text{Re}(X) = \begin{bmatrix} 1 & \omega_k \text{Im}(G_1) & -\text{Re}(G_1) \\ \vdots & \vdots & \vdots \\ 1 & \omega_k \text{Im}(G_k) & -\text{Re}(G_k) \end{bmatrix}, \text{ and} \quad (61)$$

$$\text{Im}(X) = \begin{bmatrix} 0 & -\omega_k \text{Re}(G_1) & -\text{Im}(G_1) \\ \vdots & \vdots & \vdots \\ 0 & -\omega_k \text{Re}(G_k) & -\text{Im}(G_k) \end{bmatrix}. \quad (62)$$

The real and imaginary portions of the expression for D above then become Equations 63 and 64, respectively:

$$\text{Re}(X)^T W \, \text{Re}(X) = \quad (63)$$

$$\begin{bmatrix} \sum_{i=1}^{k} w_i & \sum_{i=1}^{k} w_i \text{Im}(G_i)\omega_i & -\sum_{i=1}^{k} w_i \text{Re}(G_i) \\ \sum_{i=1}^{k} w_i \text{Im}(G_i)\omega_i & \sum_{i=1}^{k} w_i \text{Im}(G_i)^2 \omega_i^2 & -\sum_{i=1}^{k} w_i \text{Im}(G_i)\text{Re}(G_i)\omega_i \\ -\sum_{i=1}^{k} w_i \text{Re}(G_i) & -\sum_{i=1}^{k} w_i \text{Im}(G_i)\text{Re}(G_i)\omega_i & \sum_{i=1}^{k} w_i \text{Re}(G_i)^2 \end{bmatrix},$$

and $$\text{Im}(X)^T W \, \text{Im}(X) = \quad (64)$$

$$\begin{bmatrix} 0 & 0 & 0 \\ 0 & \sum_{i=1}^{k} w_i \text{Re}(G_i)^2 \omega_i^2 & \sum_{i=1}^{k} w_i \text{Im}(G_i)\text{Re}(G_i)\omega_i \\ 0 & \sum_{i=1}^{k} w_i \text{Im}(G_i)\text{Re}(G_i)\omega_i & \sum_{i=1}^{k} w_i \text{Im}(G_i)^2 \end{bmatrix}.$$

Combining these terms gives the final expression for the D matrix. This matrix will contain only real values, as shown in Equation 65 as follows:

$$D = \begin{bmatrix} \sum_{i=1}^{k} w_i & \sum_{i=1}^{k} w_i \text{Im}(G_i)\omega_i & -\sum_{i=1}^{k} w_i \text{Re}(G_i) \\ \sum_{i=1}^{k} w_i \text{Im}(G_i)\omega_i & \sum_{i=1}^{k} w_i (\text{Re}(G_i)^2 + \text{Im}(G_i)^2)\omega_i^2 & 0 \\ -\sum_{i=1}^{k} w_i \text{Re}(G_i) & 0 & \sum_{i=1}^{k} w_i (\text{Re}(G_i)^2 + \text{Im}(G_i)^2) \end{bmatrix}. \quad (65)$$

The same approach can be taken to find an expression for the b vector in terms of G and ω. The real and imaginary parts of y are illustrated in Equation 66-67.

$$\text{Re}(y) = \begin{bmatrix} -\text{Re}(G_1)\omega_1^2 \\ \vdots \\ -\text{Re}(G_k)\omega_k^2 \end{bmatrix}, \text{ and} \quad (66)$$

$$\text{Im}(y) = \begin{bmatrix} -\text{Im}(G_1)\omega_1^2 \\ \vdots \\ -\text{Im}(G_k)\omega_k^2 \end{bmatrix}. \quad (67)$$

Combining these two gives the expression for the b vector illustrated in Equation 68 as follows:

$$b = \text{Re}(X)^T W \text{ Re}(y) + \quad (68)$$

$$\text{Im}(X)^T W \text{ Im}(y) = \begin{bmatrix} -\sum_{i=1}^{k} w_i \text{Re}(G_i)\omega_i^2 \\ 0 \\ \sum_{i=1}^{k} w_i(\text{Re}(G_i)^2 + \text{Im}(G_i)^2)\omega_i^2 \end{bmatrix}.$$

The next step is to invert the D matrix. The matrix is symmetric and positive-definite so the number of computations needed to find the inverse will be reduced from the general 3×3 case. The general expression for a matrix inverse is shown in Equation 69 as:

$$D^{-1} = \frac{1}{\det(D)} adj(D). \quad (69)$$

If D is expressed as in Equation 70:

$$D = \begin{bmatrix} d_{11} & d_{12} & d_{13} \\ d_{12} & d_{22} & 0 \\ d_{13} & 0 & d_{33} \end{bmatrix}, \quad (70)$$

then the adjugate matrix can be written as in Equation 71 as follows:

$$adj(D) = \quad (71)$$

$$\begin{bmatrix} \begin{vmatrix} d_{22} & 0 \\ 0 & d_{33} \end{vmatrix} & -\begin{vmatrix} d_{12} & 0 \\ d_{13} & d_{33} \end{vmatrix} & \begin{vmatrix} d_{12} & d_{22} \\ d_{13} & 0 \end{vmatrix} \\ -\begin{vmatrix} d_{12} & d_{13} \\ 0 & d_{33} \end{vmatrix} & \begin{vmatrix} d_{11} & d_{13} \\ d_{13} & d_{33} \end{vmatrix} & -\begin{vmatrix} d_{11} & d_{12} \\ d_{13} & 0 \end{vmatrix} \\ \begin{vmatrix} d_{12} & d_{13} \\ d_{22} & 0 \end{vmatrix} & -\begin{vmatrix} d_{11} & d_{13} \\ d_{12} & 0 \end{vmatrix} & \begin{vmatrix} d_{11} & d_{12} \\ d_{12} & d_{22} \end{vmatrix} \end{bmatrix} = \begin{bmatrix} a_{11} & a_{12} & a_{13} \\ a_{12} & a_{22} & a_{23} \\ a_{13} & a_{32} & a_{33} \end{bmatrix}.$$

Due to symmetry, only the upper diagonal matrix needs to be calculated. The Determinant can then be computed in terms of the adjugate matrix values, taking advantage of the zero elements in the original array as illustrated in Equation 72 as follows:

$$\det(D) = a_{12}d_{12} + a_{22}d_{22} \quad (72).$$

Finally, the inverse of D can be written in the form shown in Equation 73:

$$D^{-1} = \frac{1}{\det(D)} adj(D). \quad (73)$$

In some embodiments, we may solve the value in Equation 74:

$$c = D^{-1}b = \frac{1}{\det(D)} adj(D)b; \quad (74)$$

So that Equation (75) is used:

$$c = \frac{1}{\det(D)} \begin{bmatrix} a_{11} & a_{12} & a_{13} \\ a_{12} & a_{22} & a_{23} \\ a_{13} & a_{32} & a_{33} \end{bmatrix} \begin{bmatrix} b_1 \\ 0 \\ b_3 \end{bmatrix} = \frac{1}{\det(D)} \begin{bmatrix} a_{11}b_1 + a_{13}b_3 \\ a_{12}b_1 + a_{23}b_3 \\ a_{13}b_1 + a_{33}b_3 \end{bmatrix}, \quad (75)$$

To get a quantitative assessment of how well the data fits the model, the original expression for the error as shown in Equation 76 is utilized:

$$e^T We = \text{Re}(y-Xc)^T W \text{ Re}(y-Xc) + \text{Im}(y-Xc)^T W \text{ Im}(y-Xc) \quad (76).$$

This can be expressed in terms of the D matrix and the b and c vectors illustrated in Equation 77:

$$e^T We = h - 2c^T b + c^T Dc \quad (77),$$

where:

$$h = \text{Re}(y^T) W \text{ Re}(y) + \text{Im}(y^T) W \text{ Im}(y) \quad (78), \text{ and}$$

$$h = \sum_{i=1}^{k} w_i (\text{Re}(G_i)^2 + \text{Im}(G_i)^2) \omega_i^4. \quad (79)$$

In some embodiments, to compare the errors from different sine sweeps, the fit error is normalized by the square of the weighted by matrix as follows in Equation 80, where h is a scalar:

$$e^T Weh^{-1} = (h - 2c^T b + c^T Dc)h^{-1} \quad (80).$$

Volume Estimation Using Swept Sine-Estimating Volume

The model fit may be used such that the resonant frequency of the port may be extracted from the sine sweep data. The delivered volume may be related to this value. The ideal relationship between the two can be expressed by the relation illustrated in Equation 81:

$$\omega_n^2 = \frac{a^2 A}{L} \frac{1}{V_2}. \quad (81)$$

The speed of sound will vary with the temperature, so it is useful to split out the temperature effects as shown in Equation 82:

$$\omega_n^2 = \frac{\gamma R A}{L} \frac{T}{V_2}. \quad (82)$$

The volume can then be expressed as a function of the measured resonant frequency and the temperature, illustrated in Equation 83 as follows:

$$V_2 = C\frac{T}{\omega_n^2}. \tag{83}$$

Where C is the calibration constant illustrated in Equation 84 as follows:

$$C = \frac{\gamma RA}{L}. \tag{84}$$

Volume Estimation Using Swept Sine-Volume Estimation Integrity Checks

In some embodiments, a second set of integrity check can be performed out of the output of the mode fit and volume estimation routines (the first set of checks is done at the FFT level). Checks may be done either through redundancy or through range checking for several values, such as: (1) model fit error, (2) estimated damping ratio, (3) estimated transfer function gain, (4) estimated natural frequency, (5) estimated variable volume, and (6) AVS sensor temperature.

In addition, portions of the AVS calculations may be done redundantly on the processor 21 of FIG. 2 using an independent temperature sensor and an independent copy of the calibration parameters to guard against RAM failures, in some specific embodiments.

Volume Estimation Using Swept Sine-Disposable Detection

The presence of the disposable, e.g., cartridges or reservoirs that are attachable, may be detected using a magnetic switch and mechanical interlock, in some specific embodiments. However, a second detection method may be used to 1) differentiate between the pump being attached to a disposable and a charger, and 2) provide a backup to the primary detection methods.

If the disposable is not present, the variable volume, $V_2$, is effectively very large. As a result, there will be a normal signal from the reference microphone, but there will be very little signal on the variable microphones. If the mean amplitude of the reference microphone during a sine sweep is normal (this verifies that the speaker is working) and the mean amplitude of the variable microphone is small, a flag is set in the processor 21 of FIG. 2 indicating that the disposable is not present.

Implementation Details—Sizing V1 Relative to V2

Sizing $V_1$ may include trading off acoustic volume with the relative position of the poles and zeros in the transfer function. The transfer function for both $V_1$ and $V_2$ are shown below relative to the volume displacement of the speaker as illustrated in Equations 85-88, as follows:

$$\frac{p_2}{v_k} = -\frac{\rho a^2}{V_1}\frac{\omega_n^2}{s^2 + 2\zeta\omega_n s + \alpha\omega_n^2}, \text{ and} \tag{85}$$

$$\frac{p_1}{v_k} = -\frac{\rho a^2}{V_1}\frac{s^2 + 2\zeta\omega_n s + \alpha\omega_n^2}{s^2 + 2\zeta\omega_n s + \omega_n^2}, \text{ where} \tag{86}$$

$$\omega_n^2 = \frac{a^2 A}{L}\frac{1}{V_2}, \zeta = \frac{fA}{2L\omega_n} \text{ and} \tag{87}$$

$$\alpha = \left(1 + \frac{V_2}{V_1}\right). \tag{88}$$

As $V_1$ is increased the gain decreases and the speaker must be driven at a higher amplitude to get the same sound pressure level. However, increasing $V_1$ has the benefit of moving the complex zeros in the $p_1$ transfer function toward the complex poles. In the limiting case where $V_1 \to \infty$ then $\alpha \to 1$ and you have pole-zero cancellation and a flat response. Increasing $V_1$, therefore, has the reduces both the resonance and the notch in the $p_1$ transfer function, and moves the $p_2$ poles toward $\omega_n$; the result is a lower sensitivity to measurement error when calculating the $p_2/p_1$ transfer function.

Implementation Details—Aliasing

Higher frequencies can alias down to the frequency of interest. The aliased frequency can be expressed in Equation 89 as follows:

$$f = |f_n - n f_s| \tag{89}$$

Where $f_s$ is the sampling frequency, $f_n$ is the frequency of the noise source, n is a positive integer, and f is the aliased frequency of the noise source.

The demodulation routine may filter out noise except at the specific frequency of the demodulation. If the sample frequency is set dynamically to be a fixed multiple of the demodulation frequency, then the frequency of the noise that can alias down to the demodulation frequency will be a fixed set of harmonics of that fundamental frequency.

For example, if the sampling frequency is 8 times the demodulation frequency then the noise frequencies that can alias down to that frequency are $$\frac{f_n}{f} = \left\{\frac{1}{n\beta+1}, \frac{1}{n\beta-1}\right\} = \left\{\frac{1}{7}, \frac{1}{9}, \frac{1}{15}, \frac{1}{17}, \frac{1}{23}, \frac{1}{25}, \cdots\right\} \tag{90}$$

$$\text{where } \beta = \frac{f_s}{f} = 8. \tag{91}$$

For $\beta = 16$ we would have the series $$\frac{f_n}{f} = \left\{\frac{1}{15}, \frac{1}{17}, \frac{1}{31}, \frac{1}{33}, \cdots\right\}. \tag{92}$$

Sources of Avs Measurement Error—Avs Chamber Movement

In some embodiments, one of the assumptions of the AVS measurement is that the total AVS volume ($V_2$ plus the volume taken up the by the other components) is constant. However, if the AVS housing flexes the total volume of the AVS chamber may change slightly and affect the differential volume measurement. In some embodiments, to keep the contribution of the volume error is kept to be less than 1.0% of the fluid delivery.

Sources of Avs Measurement Error—External Noise

In some embodiments, external noise sources may be filtered out.

Sources of Avs Measurement Error—Mechanical Shock

Mechanical shock to the pump housing during an AVS measurement will affect the microphone measurements and may result in an error in the frequency response data. This error, however, is detectable using the out-of-band variance check in the demodulation routine by the processor 21 of FIG. 2. If such an error is detected, the data point can be repeated (e.g., another sample is taken) resulting in little or no effect on the resulting AVS measurement.

Sources of Avs Measurement Error—Air in the AVS Chamber

A mechanism for an air bubble to affect the AVS measurement is through a secondary resonance. This secondary resonance will make the system $4^{th}$ order and, depending on the frequency and magnitude of the secondary resonance, can cause some error if the estimation is using a $2^{nd}$ order model.

Sources of Avs Measurement Error—Electrical Component Failure

In general, failure an electrical component will result in no signal or in increased harmonic distortion. In either case the fault would be detected by AVS integrity checks and the measurement invalidated.

The one exception that has been identified is a failure of the oscillator used to control the DAC and ADC. If this oscillator were to drift out of tolerance it would introduce a measurement error that would not be detected by the low-level integrity check (it would be detected in an extreme case by the volume integrity checks described above). To guard against these failures, in some embodiments, the oscillator is checked against an independent clock whenever an AVS measurement is initiated.

What is claimed is:

1. A pump, comprising:
   a reservoir configured to deliver a fluid;
   a port coupled to the reservoir and configured to discharge the fluid;
   a plunger having a piston coupled to a shaft, wherein the piston is disposed within the reservoir in sliding engagement with an inner surface of the reservoir, wherein the piston defines a first side of the reservoir and a second side of the reservoir whereby movement of the plunger towards the first side of the reservoir discharges fluid through the port; and
   a reference-volume assembly coupled to the reservoir, wherein the reference-volume assembly comprises:
      a reference-volume chamber in acoustic communication with the second side of the reservoir;
      a speaker disposed within the reference-volume chamber; and
      a reference microphone disposed within the reference-volume chamber,
      wherein the reference-volume assembly further comprises a conduit configured to receive the shaft, wherein the shaft is in sliding engagement with the conduit.

2. The pump according to claim 1, wherein the reference-volume assembly is coupled to the reservoir at an opposite end of the reservoir relative to the port.

3. The pump according to claim 2, further comprising a variable-volume microphone disposed within the reservoir configured to sense a sound wave within the reservoir, the sound wave originating from the speaker.

4. The pump according to claim 1, further comprising:
   an additional reservoir configured to deliver an additional fluid;
   an additional port coupled to the additional reservoir and configured to discharge the additional fluid; and
   an additional plunger having an additional piston coupled to an additional shaft, wherein the additional piston is disposed within the additional reservoir in sliding engagement with an inner surface of the additional reservoir, wherein the additional piston defines a first side of the additional reservoir and a second side of the additional reservoir whereby movement of the additional plunger towards the first side of the additional reservoir discharges fluid through the additional port; wherein the reference-volume assembly is further coupled to the additional reservoir at an opposite end of the additional reservoir relative to the additional port, wherein the reference-volume chamber is further in acoustic communication with the second side of the additional reservoir.

5. The pump according to claim 4, wherein at least one of the first and second reservoirs are attachable to the reference-volume assembly.

6. The pump according to claim 5, further comprising a manifold, the manifold comprising:
   a first connector port coupled to the port;
   a second connector port coupled to the additional port; a discharge port; and
   a fluid path fluidly connecting together the first and second connector ports to the discharge port.

7. The pump according to claim 6, wherein the manifold is attachable to the first and second connector ports.

8. The pump according to claim 4, further comprising a variable-volume microphone disposed within the reservoir configured to sense a sound wave within the reservoir.

9. The pump according to claim 8, further comprising an additional variable-volume microphone disposed within the additional reservoir configured to sense the sound wave within the additional reservoir.

10. The pump according to claim 4, further comprising a variable-volume microphone disposed on the reference-volume assembly configured to sense a sound wave within the reservoir.

11. The pump according to claim 10, further comprising an additional variable-volume microphone disposed on the reference-volume assembly configured to sense the sound wave within the additional reservoir.

12. The pump according to claim 1, further comprising: a linear position sensor configured to sense a position of the shaft.

13. The pump according to claim 12, further comprising a housing, wherein the linear position sensor is disposed within the housing.

14. The pump according to claim 1, further comprising a housing, wherein the reservoir is disposed within the housing; and wherein the plunger is disposed within the housing.

15. The pump according to claim 1, further comprising an actuator coupled to the shaft to actuate the plunger.

16. The pump according to claim 15, further comprising a housing, wherein the actuator is disposed within the housing.

17. The pump according to claim 1, wherein the piston comprises a seal disposed along a periphery of the piston.

18. The pump according to claim 1, wherein the plunger is moveable between a fully discharged position and a fully loaded position, wherein the reference-volume chamber is in fluid communication with the second side of the reservoir when the plunger is positioned anywhere between the fully discharged position and the fully loaded position.

19. The pump according to claim 1, wherein the conduit further comprises a seal configured to receive the shaft and acoustically seal the second side of the reservoir as the shaft engages with the conduit.

20. The pump according to claim 1, wherein the reference-volume assembly further comprises an acoustic port in acoustic communication with the reference-volume chamber and the second side of the reservoir.

* * * * *